United States Patent
Keys et al.

(10) Patent No.: US 6,211,139 B1
(45) Date of Patent: Apr. 3, 2001

(54) POLYESTER POLYQUATERNARY COMPOUNDS, COMPOSITIONS CONTAINING THEM, AND USE THEREOF

(75) Inventors: Robert O. Keys, Columbus; Floyd E. Friedli, Dublin; Damon M. Dalrymple, Columbus; Monna Manning, Columbus; Craig Poffenberger, Columbus, all of OH (US); David E. Whittlinger, Janesville, WI (US); Wangqi Hou, Dublin, OH (US)

(73) Assignee: Goldschmidt Chemical Corporation, Hopewell, VA (US)

( * ) Notice: Subject to any disclaimer, the term of this patent is extended or adjusted under 35 U.S.C. 154(b) by 0 days.

(21) Appl. No.: 09/170,623

(22) Filed: Oct. 13, 1998

Related U.S. Application Data

(63) Continuation-in-part of application No. 08/845,676, filed on Apr. 25, 1997, now abandoned, which is a continuation-in-part of application No. 08/638,615, filed on Apr. 26, 1996, now abandoned.

(51) Int. Cl.$^7$ .............................. C11D 1/62; C11D 1/645; C11D 1/65; C11D 1/835
(52) U.S. Cl. ............................................ 510/504
(58) Field of Search ............................................ 510/504

(56) References Cited

U.S. PATENT DOCUMENTS

| | | |
|---|---|---|
| 2,878,144 | 3/1959 | Conbere et al. . |
| 2,967,755 | 1/1961 | Keller et al. . |
| 2,970,158 | 1/1961 | Levis et al. . |
| 3,170,938 | 2/1965 | Levis et al. . |
| 4,126,562 | 11/1978 | Goffinet et al. . |
| 4,155,855 | 5/1979 | Goffinet et al. . |
| 4,439,331 | 3/1984 | Billenstein et al. . |
| 4,442,013 | 4/1984 | Fraikin et al. . |
| 4,743,304 | 5/1988 | Gilmore et al. ................. 106/281 N |
| 4,851,139 | * 7/1989 | Lewis et al. ......................... 252/8.8 |
| 4,973,422 | * 11/1990 | Schmidt ........................ 252/174.11 |
| 5,173,200 | * 12/1992 | Kellett ................................. 252/8.8 |
| 5,368,755 | * 11/1994 | Chavez et al. ........................ 252/8.6 |
| 5,538,595 | 7/1996 | Trokham et al. . |
| 5,725,736 | 3/1998 | Schroeder et al. . |
| 5,767,062 | 6/1998 | Trinh et al. . |
| 5,783,544 | 7/1998 | Trinh et al. . |

FOREIGN PATENT DOCUMENTS

| | | |
|---|---|---|
| 267921 | 2/1961 | (AU) . |
| 645855 | 7/1962 | (CA) . |
| 3135014 | 4/1981 | (DE) . |
| 3127239 | 10/1981 | (DE) . |
| 0360181 | 3/1990 | (EP) . |
| 0461419 | 12/1991 | (EP) . |
| 0643038 | 3/1995 | (EP) . |
| 0803498 | 10/1997 | (EP) . |
| 767596 | 2/1957 | (GB) . |
| 866408 | 4/1961 | (GB) . |
| 5331118 | 12/1993 | (JP) . |
| 6212567 | 8/1994 | (JP) . |
| 6256272 | 9/1994 | (JP) . |
| 6340598 | 12/1994 | (JP) . |
| 718571 | 1/1995 | (JP) . |
| 96/03970A1 | 2/1996 | (WO) . |
| 9717695 | 5/1997 | (WO) . |
| 9717696 | 5/1997 | (WO) . |

OTHER PUBLICATIONS

Chemical Abstract 107468F—Textile treatment with cationic agents and electrolytes, 1969 (No Month Available).

* cited by examiner

Primary Examiner—John Hardee
(74) Attorney, Agent, or Firm—Scully, Scott, Murphy & Presser

(57) ABSTRACT

A composition comprising: (a) a compound of the following structural formula:

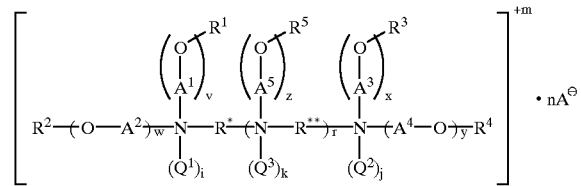

wherein each of R* and R** is independently a linear, branched or cyclic alkylene group containing 2 to 12 carbon atoms, wherein no two nitrogen atoms are separated by fewer than 2 carbon atoms; each of $A^1$, $A^2$, $A^3$, $A^4$, and $A^5$ is independently a straight or branched alkylene containing 2 to 4 carbon atoms; each of $R^1$, $R^2$, $R^3$, $R^4$, and $R^5$ is independently —H or $R^A C(O)$— wherein $R^A$ is straight or branched alkyl or alkenyl containing 7 to 21 carbon atoms and 0 to 4 carbon-carbon double bonds; provided that at least one of $R^1$, $R^2$, $R^3$, $R^4$, or $R^5$ is $R^A C(O)$—; each of $Q^1$, $Q^2$ and $Q^3$ is independently —H, —$CH_3$, —$C_2H_5$, —$C_3H_7$, —$C_4H_5$, benzyl, —$CH_2COOH$, or —$CH_2COOA^-$; or, if R* is a —$CH_2CH_2$— group, $Q^1$ and $Q^3$ together or $Q^1$ and $Q^2$ together may be a —$CH_2CH_2$— group to form a six-membered piperazine ring; or, if R** is a —$CH_2CH_2$— group, $Q^3$ and $Q^3$ together may be a —$CH_2CH_2$— group to form a six-membered piperazine ring; m is 0 to 4; r is 0 to 2; each of v, w, x, y, and z is independently 1 to 8; i is 0 to 1, j is 0 to 1, and each k is 0 to 1, and the sum of (i+j+k) is 0 to 4; each $A^-$ is independently an anion as defined below; and n is the number of moles of $A^-$ needed to give the compound of structural formula (1) a zero net charge; and water, wherein the composition does not contain a significant amount of textile resin treating compounds.

17 Claims, No Drawings

POLYESTER POLYQUATERNARY COMPOUNDS, COMPOSITIONS CONTAINING THEM, AND USE THEREOF

This application is a continuation-in-part of U.S. application Ser. No. 08/845,676, filed Apr. 25, 1997, now abandoned which is a continuation-in-part of U.S. application Ser. No. 08/638,615, filed Apr. 26, 1996 now abandoned.

BACKGROUND OF THE INVENTION

The present invention relates to amine and quaternary ammonium compounds and formulations thereof useful as, for instance, fabric softeners, paper debonders, hair conditioners, skin conditioners, paper deinking and ink floatation agents, asphalt emulsion agents, corrosion inhibitor agents, ore floatation agents, pesticide emulsion agents, car drying aid sprays, drilling fluid additives, and the like.

Heretofore quaternary ammonium compounds and a very few dialkyl ammonium compounds ("conventional quats") have found widespread use in many applications. For example, a variety of conventional quats have been proposed for many uses, for example, in fabric softeners for home use or for industrial and institutional use. In general, such compounds exhibit properties which present some difficulty in the manufacture, formulation use, aesthetic properties, biodegradability, and environmental compatibility of these compositions. For example, many of the conventional compositions used for these functions, even if completely biodegradable with time, do not biodegrade as rapidly as could be desired and are thus not considered readily biodegradable. In addition, several of the commercial readily biodegradable softeners, conditioners, and debonders do not function as effectively as the conventional products that are less biodegradable. Thus, to maintain effective levels of performance, increased amounts of such less effective, more readily biodegradable products (such as softeners) must be employed and, as will be readily apparent, this factor decreases the cost-effectiveness of the product.

In addition, the color and the odor of the products using conventional quats also pose problems with many biodegradable raw materials. Light color and low odor are essential to obtaining customer acceptance and to achieving stable and acceptable long-term product aesthetic properties. Such properties are difficult to achieve with conventional quats. Moreover, there is increasing interest in obtaining fabric softener and personal care formulations which are clear (translucent or transparent) liquids, even to the point of obtaining a crystal-clear dispersion when the formulation is dispensed and dispersed into rinse water (even at levels of 50–100 ppm actives in water). Clear formulations may also offer several performance advantages, depending on the application, for example, clear fabric softeners offer reduced staining of the fabric, improved dispersibility, and greatly improved rewetting of the fabric or other substrate. Discovery of such clear compositions requires careful identification of proper quaternary and/or polyquaternary ammonium compounds, together with appropriate additives, such as solvents and cosolvents, which act together to achieve the desired appearance.

The relatively poor solubility of conventional quats also contributes to certain difficulties that will vary, depending on the application. For example, when such conventional quats are used in fabric softeners, their poor solubility inhibits the dispersibility of the fabric softener actives into water and the dispersibility of the formulated fabric softener product into the washing machine.

Thus, there remains a need for identification of new amine and ammonium derivatives, and particular diquaternary and polyquaternary derivatives, which are useful as fabric softeners and which are also biodegradable, highly effective in softening, debonding, conditioning, and the like, and yet avoid these problems upon manufacture, formulation and use. It is also desirable for the active agents used in hair and skin conditioners, paper debonding compositions, textile softeners, and the like, to be readily biodegradable and to exhibit a satisfactorily high activity. Conventional products have to date not been able to exhibit both properties to a high degree, thus necessitating acceptance of reduced biodegradability or reduced activity. There is thus still a need for compounds exhibiting levels of activity as conditioners, paper debonders, and so on, as the case may be, which are comparable or superior to conventionally employed actives, such as conventional quats, while also exhibiting ready biodegradability.

Certain polyquaternary ammonium compounds have been disclosed. For example, Conbere et al., U.S. Pat. No. 2,878,144, discloses the use of certain diquaternary ammonium compounds for use as softening and antistatic agents for use in aqueous textile resin treating baths (see, in particular, col. 2, lines 50–65). Conbere et al., however, discloses no actual examples of the use of diquaternary compounds in aqueous textile resin treating baths, does not provide any formulations incorporating such diquaternary compounds, nor mentions or suggests the use of such diquaternary compounds in any application other than for textile fabric treatment using aqueous textile resin treating baths, which use is very different from the applications disclosed and claimed herein. Moreover, the disclosure of Conbere et al. is limited to diquaternary compounds, whereas the instant application and claims include amines and triquats and tetraquats.

Schroeder et aL, U.S. Pat. No. 5,725,736, discloses the incorporation of certain silicone betaines into tissue to improve the softness thereof. Schroeder et al. also discloses the optional use of certain polyquaternary ammonium compounds in combination with the silicone betaines of the invention. Schroeder et al., however, discloses no actual examples of the use of polyquaternary compounds in the method of the invention, does not provide any formulations incorporating such polyquaternary compounds, nor mentions or suggests the use of such polyquaternary compounds in any application other than tissue softening and only in combination with certain silicone betaines.

As can be appreciated, the chemistry of fabric softeners, paper debonders, hair conditioners, skin conditioners, textile softeners, car wax sprays, and the like is challenging. Each of these applications presents its own complications, because the interactions between the various components of the compositions must be considered in addition to the individual chemistry of each component.

For example, considering the fabric softening application, the detergent compounds with the widest range of cleaning properties are generally anionic (negatively charged) surfactants. Such anionic surfactants, for example, may include the alkylbenzene sulfonates, α-olefin sulfonates, and xylene sulfonates available from Witco Corporation under the WITCONATE® trademark. In contrast, as exemplified by the amine and ammonium compounds discussed above, fabric softening compounds are generally cationic (positively charged). Thus, when the anionic detergent ingredients and cationic softening ingredients are present in the same aqueous solution, they have a natural tendency to complex together or even precipitate out of solution. This complexation or precipitation reaction interferes with the performance of both the detergent compounds and the softening compounds and is therefore undesirable. It can be readily appreciated that this undesirable complexation or precipitation reaction may occur if both detergent and softener compounds are added together in a wash cycle; however, as North American washing machines typically rinse the clothes only once before fabric softener is added to the washload, even if the fabric softener is added during a rinse cycle (as is typically done), residual anionic detergent compounds (including builders) present in the fabric complexes with the cationic softener compounds.

SUMMARY OF THE INVENTION

The present invention achieves these objectives and also exhibits the properties and advantages described herein.

One aspect of the present invention comprises compounds of the following structural formula (hereinafter "structural formula (1)"):

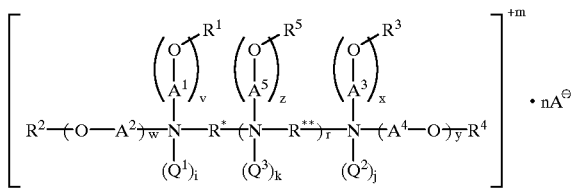

wherein each of R* and R** is independently a linear, branched or cyclic alkylene group containing 2 to 12 carbon atoms, wherein no two nitrogen atoms are separated by fewer than 2 carbon atoms;

each of $A^1, A^2, A^3, A^4$, and $A^5$ is independently a straight or branched alkylene containing 2 to 4 carbon atoms;

each of $R^1, R^2, R^3, R^4$, and $R^5$ is independently —H or $R^A C(O)$— wherein $R^A$ is straight or branched alkyl or alkenyl containing 7 to 21 carbon atoms and 0 to 4 carbon-carbon double bonds; provided that at least one of $R^1, R^2, R^3, R^4$, or $R^5$ is $R^A C(O)$—;

each of $Q^1, Q^2$ and $Q^3$ is independently —H, —CH$_3$, —C$_2$H$_5$, —C$_3$H$_7$, —C$_4$H$_5$, benzyl, —CH$_2$COOH, or —CH$_2$COOA$^-$; or, if R* is a —CH$_2$CH$_2$— group, $Q^1$ and $Q^3$ together or $Q^1$ and $Q^2$ together may be a —CH$_2$CH$_2$— group to form a six-membered piperazine ring; or, if R** is a —CH$_2$CH$_2$— group, $Q^3$ and $Q^3$ together may be a —CH$_2$CH$_2$— group to form a six-membered piperazine ring;

m is 0 to 4;

r is 0 to 2;

each of v, w, x, y, and z is independently 1 to 8;

i is 0 to 1, j is 0 to 1, and each k is 0 to 1, and the sum of (i+j+k) is 0 to 4;

each A$^-$ is independently an anion as defined below; and n is the number of moles of A$^-$ needed to give the compound of structural formula (1) a zero net charge.

In a preferred embodiment of the invention, the composition includes water in the formulation. In another preferred embodiment of the invention, the formulation does not contain a significant amount of silicone betaines or any silicone betaines. In a further preferred embodiment of the invention, the formulation does not contain a significant amount of silicone compounds or any silicone compounds. In yet another preferred embodiment of the invention, the formulation does not contain a significant amount of textile resin treating compounds or any textile resin treating compounds.

In another preferred embodiment of the invention, the composition comprises a mixture of two or more different compounds of structural formula (1). In a preferred embodiment of the invention, m is from about 1 to 4, more preferably 2 to 4, and most preferably 3 to 4.

Another embodiment of the invention comprises compounds of structural formula (1) is compounds wherein at least one of v, w, x, y, and z is greater than 1. In a preferred embodiment of the invention, each of v, w, x, y, and z is greater than 1. Another embodiment of the invention includes compounds of structural formula (1) wherein substituents $Q^1, Q^2$ and $Q^3$ are not present, or there is one or more substituents selected from $Q^1, Q^2$ and $Q^3$ and any such substituent present is —H. Another embodiment of the present invention further comprises an amine salt, polyamine salt, or mixture thereof. Yet another embodiment of the present invention comprises liquid compositions, useful for instance as fabric softeners, comprising (a) a component selected from the group consisting of compounds of structural formula (1) and mixtures thereof; (b) water; and (c) optionally, one or more solvents or cosolvents.

Another aspect of the present invention comprises a composition comprising:

(a) a compound of structural formula (1); and (b) a second surfactant selected from the group consisting of anionic surfactants, cationic surfactants, zwitterionic surfactants, nonionic surfactants, amphoteric surfactants, and blends thereof.

In an embodiment of the present invention, the composition further comprises water. In an embodiment of the present invention, the second surfactant comprises a conventional quaternary compound. In another embodiment of the present invention, the composition does not contain a significant amount of silicones. In yet another embodiment of the present invention, the composition comprises a mixture of two or more different compounds of structural formula (1). In a further embodiment of the present invention, the composition comprises a mixture of two or more different conventional quaternary compounds.

In an embodiment of the present invention, the secondary surfactant is selected from the group consisting of: alkylbenzene sulfonates, α-olefin sulfonates, and xylene sulfonates. In another embodiment of the present invention, the secondary surfactant is selected from the group consisting of: nonylphenol ethoxylates; $C_5$–$C_{20}$ linear or branched alcoxylates using EO, PO, iPO, BO, or mixtures thereof; amine ethoxylates; fatty amide ethoxylates; fatty acid ethoxylates; carboxylated nonionics; α-polyglucosides; and mixtures thereof. In a further embodiment of the present invention, the secondary surfactant is selected from the group consisting of: ammonium lauryl sulfate, sodium lauryl sulfate, any α-olefin sulfonate, ammonium laureth sulfate (2 or 3 moles), sodium laureth sulfate (2 or 3 moles), sodium myristyl sulfate, sodium myristeth sulfate (1–4 moles), ammonium xylene sulfonate, sodium xylene sulfonate, TEA dodecylbenzene sulfonate, TEA lauryl sulfate, ammonium pareth sulfate, sodium pareth sulfate, sodium oleth sulfate, derivatives thereof, and mixtures thereof. In another embodiment of the present invention, the secondary surfactant is selected from the group consisting of: betaines, sulfosuccinates, mono- and diglycerides, glycinates, sugars and derivatives thereof, hydroxysultaines, mono- and diacetates, ethoxylated derivatives thereof, and mixtures thereof. In a further embodiment of the present invention, the secondary surfactant is selected from the group consisting of: cocamidopropyl betaine, lauramidopropyl betaine, ricinoleamidopropyl betaine, myristamidopropyl betaine, palmamidopropyl betaine, stearamidopropyl betaine, behenamidopropyl betaine, erucamidopropyl betaine, cocamidopropyl hydroxysultaine, myristamidopropyl hydroxysultaine, palmamidopropyl hydroxysultaine, stearamidopropyl hydroxysultaine, behenamidopropyl hydroxysultaine, erucamidopropyl hydroxysultaine, disodium lauroamphodiacetate, disodium cocamphodiacetate, disodium myristamphodiacetate, disodium palmamphodiacetate, disodium stearamphodiacetate, disodium behenamphodiacetate, disodium erucamphodiacetate, sodium lauryl amphoacetate, sodium cocamphoacetate, sodium cocoamphopropionate, sodium laurylamphopropionate, disodium lauroamphodipropionate, sodium lauryl sulfosuccinate, disodium laureth sulfosuccinate, cocobetaine, laurylbetaine, myristylbetaine, stearylbetaine, behenylbetaine, PEG 1-300 glyceryl cocoate, PEG 1-300 glyceryl tallowate, PEG 1-500 hydrogenated glyceryl palmitate, coco-glucoside, lauryl glucoside, decyl glucoside, and mixtures thereof. In yet another embodiment of the present invention, the secondary surfactant is an alkanolamide. In an embodiment of the present invention, the secondary surfactant is an amine oxide.

A further aspect of the present invention comprises a composition comprising:

(a) a compound of structural formula (1);

(b) a solvatrope or coupling agent or blends thereof; and (c) an oil or hydrophobic organic component and blends thereof.

In an embodiment of the present invention, the composition further comprises water. In another embodiment of the present invention, the amount of the compound of structural formula (1) is about 0.1 wt. % to about 65 wt. % of the formulation; the amount of solvatrope or coupling agent is about 0.1 wt. % to about 65 wt. % of the formulation, the amount of oil or hydrophobic organic component is about 0.1 wt. % to 65 wt. % of the formulation, and the amount of water is about 20 to 99.7 wt. % of the formulation, preferably about 35 wt. % to about 99.7 wt. %. In another embodiment of the present invention, the solvatrope or coupling agent is selected from the group consisting of: hydroxypivalyl hydroxypivalate and its alkoxylated derivatives, TMPD, TMPD alkoxylates, ethanol, isopropanol, butanol, 1,2-cyclohexanedimethanol, 1,4-cyclohexanedimethanol, HPHP glycol, isopentyldiol, 1,2-hexanediol, ethylene glycol butyl ether, hexylene glycol, isoprene glycol, sorbitan ethoxylates, 2-butoxyethanol, $C_6$–$C_{12}$ diols/triols and ester diols/triols and their alkoxylated derivatives, glycol ethers, and mixtures thereof. In yet another embodiment of the present invention, the oil or hydrophobic organic component is selected from the group consisting of: fatty acids; fatty amides; fatty alcohols; fatty oils; fatty esters made from a $C_8$–$C_{22}$ fatty acid and a $C_1$–$C_8$ alcohol; dialkyl esters; mineral oil; mineral seal oils; silicone oils; petrolatums; monoglycerides; diglycerides; triglycerides; aliphatic, paraffinic, and naphthalinic hydrocarbons; oils and spirits; and mixtures thereof. In other embodiments of the present invention, the composition comprises a mixture of two or more different compounds of structural formula (1) or a mixture of two or more different solvents or coupling agents. In another embodiment of the present invention, the iodine value of the fatty acid used to make the compound of structural formula (1) ranges from about 30 to about 140, preferably from about 80 to about 120, most preferably, from about 90 to about 110.

In an embodiment of the present invention, the composition further comprises a personal care emollient which may be selected from the group consisting of: acetylated lanolin, aminopropyl dimethicone, ammonium hydrolyzed collagen, ammonium lauroyl sarcosinate, amodimethicone, amodimethicone/dimethicone copolyol, amodimethicone hydroxystearate, capryloyl hydrolyzed collagen, cetyl alcohol, cetyl esters, cetyl laurate, cocamidopropyl dimethylamine dihydroxymethylpropionate, cocoyl hydrolyzed soy protein, collagen, disodium cocoamphodiacetate, disodium cocoamphodipropionate, dioctyl dimerate, ditridecyl adipate, glycerine, glyceryl oleate, glyceryl stearate, hydrogenated soybean oil, hydrogenated tallow glycerides, isocetyl stearate, jojoba (*Buxus chinensis*) oil, keratin, lanolin, milk protein, mineral oil, oat (*Avena sativa*) protein, octyl cocoate, oleyl myristate, oleyl stearate, palm alcohol, palm glycerides, panthenol, PEG-10, PEG-32, PEG-100, PEG-200, petrolatum, PPG-6-sorbeth-245, stearyl citrate, tridecyl stearate, urea. vegetable oil, wheat amino acids, and mixtures thereof.

In another embodiment of the present invention, the composition further comprises a personal care emulsifier, which may be selected from the group consisting of: beheneth-5, beheneth-10, beheneth-20, butylglucoside caprate, ceteareth-2, ceteareth-10, ceteareth-18, ceteth-10, ceteth-16, corn oil PEG-8 esters, $C_{9-11}$ pareth-3, $C_{11-15}$ pareth-5, $C_{11-15}$ pareth-12, $C_{12-13}$ pareth-2, $C_{12-13}$ pareth-10, $C_{12-13}$ pareth-15, deceth-4, deceth-5, deceth-6, di-$C_{12-13}$ pareth-6 phosphate, di-$C_{12-15}$ pareth-8 phosphate, glyceryl cocoate, glyceryl laurate, glyceryl oleate, isoceteth-10, isodeceth-6, isosteareth-10, laureth4, laureth-5, laureth-10, octyldodeceth-10, octyldodeceth-20, oleoyl ethyl glucoside, oleth-2, oleth-4, PEG-8 caprate, PEG-8 castor oil, PEG-7 cocamide, PEG-11 cocamide, PEG-15 cocoate, PEG-20 dilaurate, PEG-32 dilaurate, PEG-8 dioleate, PEG-2 distearate, PEG-8 distearate, PEG-8 glyceryl laurate, PEG-15 glyceryl laurate, PEG-4 isostearate, PEG-4 laurate, PEG-5 octanoate, PEG-9 oleamide, PEG-5 oleate, PEG-20 palmitate, PEG-6 stearate, PEG-16 tallate, polysorbate 20, polysorbate 80, steareth-10, trideceth-5, undeceth-9, and mixtures thereof.

In an embodiment of the present invention, the composition is emulsified into a microemulsion. In another embodiment of the present invention, the composition is clear. In yet another embodiment of the present invention, the amount of the compound of structural formula (1) is about 5 wt. % to about 50 wt. % of the formulation, preferably about 10 wt. % to about 30 wt. %, and most preferably about 15 wt. % to about 25 wt. %; the amount of solvatrope or coupling agent is about 2 wt. % to about 15 wt. % of the formulation, preferably about 3 wt. % about 10 wt. %, and most preferably about 6 wt. % to about 10 wt. %; the amount of oil or hydrophobic organic component is about 5 wt. % to 50 wt. % of the formulation, preferably about 10 wt. % to about 30 wt. %, and most preferably about 15 wt. % to about 20 wt. %; and the amount of water is about 10 to 70 wt. % of the formulation, preferably about 20 wt. % to about 60 wt. %, and most preferably about 30 wt. % to about 50 wt. %.

In an embodiment of the present invention, the composition is used as a personal care formulation, wherein the amount of the compound of structural ormula (1) is about 0.1 wt. % to about 65 wt. % of the formulation, preferably about 0.1 wt. % to about 25 wt. %, and most preferably about 0.1 wt. % to about 5 wt. %; the amount of solvatrope or coupling agent is about 0.1 wt. % to about 65 wt. % of the formulation, preferably about 0.1 wt. % about 25 wt. %, and most preferably about 0.1 wt. % to about 0.5 wt. %; the amount of oil or hydrophobic organic component is about 0.1 wt. % to 65 wt. % of the formulation, preferably about 0.1 wt. % to about 25 wt. %, and most preferably about 0.1 wt. % to about 5 wt. %; and the amount of water is about 20 to 99.7 wt. % of the formulation, preferably about 35 wt. % to about 99.7 wt. %, and most preferably about 65 wt. % to about 99.7 wt. %.

In another embodiment of the present invention, the composition is a pesticide emulsion agent formulation further comprising water. In yet another embodiment of the present invention, the composition is a pesticide formulation comprising the pesticide emulsion agent formulation and an effective amount of pesticide. In another embodiment of the present invention, the pesticide formulation comprises an amount of compound of structural formula (1) ranging from about 5 wt. % to about 50 wt. %, preferably from 10 wt. % to about 40 wt. %, of the pesticide formulation.

Other aspects of the instant invention include using the compounds of structural formula (1) either alone or in formulations, as a fabric softener (either alone or in a combination detergent/fabric softener), as a car spray microemulsion, as a paper debonder, as a hair or skin conditioner, as a corrosion inhibitor, as an asphalt emulsifier, as an organoclay ingredient, or as an agricultural product emulsifier. The polyethoxylated compounds of structural formula (1) may also find uses as textile treatments, particularly when used in conjunction with a resin bath. Other aspects of the present invention include such methods and processes using the compounds of structural formula (1) either alone or in formulations.

It can be seen from the above, that ranges in amounts given for each ingredient or component of a composition or formulation set forth herein in certain circumstances may be theoretically capable of adding up to a sum of greater than 100%. As would be appreciated by those of skill in the art, it is understood that such impossible formulations (that is, those formulations whose component amounts add to a sum greater than 100%) are excluded from the claims and disclosure. For example, a formulation having components A and B, where the amount of A is said to range from 25% to 75% and the amount of B is said to range from 25% to 55%, if containing 65% of A, is understood to have 35% or less of B in that formulation, so that the sum of A and B does not exceed 100%. Thus, all formulations or compositions presented herein whose component amounts add to a sum less than or equal to 100% are understood as being part of the claims and disclosure.

DETAILED DESCRIPTION OF THE INVENTION

The present invention is directed to novel polyester amine compounds and polyester polyquaternary compounds, compositions and formulations containing such novel compounds, and uses thereof.

A. PREFERRED COMPOUNDS AND COMPOSITIONS

As will be appreciated, a particularly preferred embodiment of the present invention comprises mixtures of compounds corresponding to structural formula (1), such that degrees of quaternization or protonation (including unquaternized, unprotonated compounds), degrees of esterification, and chain lengths and molecular weights of different molecules within the mixture will differ such that the respective properties can be represented as an average over all the molecules present in the mixture. In such mixtures, then, properties such as the degree of quaternization can be expressed as average values which may lie between integer whole numbers.

Referring to structural formula (1), the groups depicted as $Q^1$, $Q^2$ and $Q^3$ represent substituents which, when present, protonate (if they are —H) or quaternize (if they are any other group) the respective nitrogen atoms to which they are bonded. While the structure of structural formula (1) embraces compounds ranging from compounds wherein no nitrogen atom is quaternized or protonated with a corresponding Q substituent, through compounds wherein every nitrogen atom is quaternized or protonated with a Q substituent, one preferred embodiment is compounds wherein the compound of structural formula (1) should be partially quaternized. The term "partially" is meant to convey that at least one nitrogen atom on the molecule as depicted in structural formula (1) does not have a Q substituent attached to it. In particular, in mixtures of compounds which are diamines (that is, in structural formula (1), the subscript r is zero), there is on average in the mixture preferably 1–2, and more preferably 1.5–2, quaternizing groups Q per molecule.

Another preferred embodiment is compounds, and mixtures thereof, in which there are either no Q substituents or the only Q substituents present are —H. Such Q substituents can be present in a degree such that all nitrogen atoms are protonated, or fewer than all nitrogen atoms are protonated ("full" and "partial" protonation, respectively). Although many of the teachings and disclosure below uses the terms "quats", "ester quats", "polyester quats", and similar language with respect to applications and formulations including compounds of structural formula (1), such disclosures should be understood to apply equally to the non-quaternized compounds according to structural formula (1), unless specifically and unambiguously excluded.

The compounds of structural formula (1) may also have any of a range of degrees of esterification, depending on the application. As shown in structural formula (1), the degree of esterification can range from 1 to 4 for diamines, and up to 5 or 6 for triamines or tetramines, respectively. The preferred degree of esterification, that is, the total number of $R^A$ groups present, preferably ranges from about 2 to about 4. This is true especially for diamines, wherein a preferred degree of esterification is from 1 to about 3 for clear, translucent formulations and about 2 to 3.5 for easily dispersible formulations, and the more preferred degree of esterification is about 2.0 to about 2.5; for triamines and tetramines the preferred degree of esterification should be adjusted accordingly; that is, approximately one additional ester group per additional amine group. In emulsifier applications, the compound of structural formula (1) is prepared having only about 1 to about 2 ester groups per molecule to ensure that the molecule as a whole is less hydrophobic than those that would typically be employed in other applications. Any desired degree of esterification can be attained by reaction between the polyhydroxy-substituted precursor and a stoichiometrically appropriate amount of the corresponding carboxylic acid(s). For instance, even a non-integer target degree of esterification such as 2.5 can be attained by reaction to form a mixture containing equal amounts of triester and diester.

The respective $R^A C(O)$— acyl groups can all have the same chain lengths. More preferably they have several chain lengths and degrees of carbon-carbon unsaturation, reflecting the fact that the fatty acyl groups can be derived from naturally occurring sources which contain mixtures of fatty acids with differing chain lengths and differing degrees of carbon-carbon unsaturation. Examples of such sources include fatty acids derived from the following sources: tallow, fish oils, canola (including fatty acids derived from partially hydrogenated canola), jojoba, palm, coconut, avocado, wheat germ, rapeseed, olive, orange, corn, linseed, neem, peanut, safflower, sesame seed, soybean, sunflower seed, and cocoa butter. Preferred materials are tallow, canola, and palm. If a clear formulation is desired, the use of an unsaturated fatty acid is preferred to make the compound of structural formula (1) or at least a portion of the compound of structural formula (1) used in the formulation. The degree of unsaturation of a compound is typically expressed as the iodine value (I.V.). If a clear formulation is desired, the I.V. of the fatty acid used to make the compound of structural formula (1) ranges from about 30 to about 140, more preferably the I.V. ranges from about 80 to about 120, most preferably the I.V. ranges from about 90 to about 110. Such clear formulations have an additional advantage: they generally exhibit excellent freeze/thaw recovery.

Referring to structural formula (1), the molecules shown can be diamines, triamines, or tetramines. For many purposes, the diamines are preferred. The R* bridge linking the two nitrogen atoms of the diamine can contain 2 to 12 carbon atoms, and preferably contains 3 to 12 carbon atoms, most preferably 6 to 10 carbon atoms. One particularly preferred R* group is an alkylene containing 6 to 12 carbon atoms, such as linear hexamethylene. Other useful groups can contain up to 10 carbon atoms between the nitrogen atoms, or anywhere from 3 to 10 carbon atoms presenting straight or branched alkylene structures.

The various moieties depicted at structural formula (1) as $A^{1-5}$ can each, independently, be ethyl, propyl (straight or branched) or butyl (straight or branched). Preferably, each of the $A^{1-5}$ groups present is the same, for ease of synthesis. It is also preferred that each of $A^{1-5}$ is ethyl or propyl (especially isopropyl).

Further preferred embodiments of compounds of structural formula (1) are described herein with respect to the various formulation capabilities of the products of this invention.

The compounds of structural formula (1), when quaternized and/or protonated to any degree, include an anion $A^-$ which is present in a number of moles equal to the total positive charge of the nitrogen-containing cation. The anion $A^-$ can represent any anion which is not deleterious to the properties of the overall compound. Non-limiting examples of $A^-$ include fluoride, chloride, bromide, iodide, chlorite, chlorate, hydroxide, hypophosphite, phosphite, phosphate, carbonate, formate, acetate, lactate, and other carboxylates, oxalate, methyl sulfate, ethyl sulfate, benzoate, and salicylate, and the like. Preferred examples are chloride, bromide, methyl sulfate, ethyl sulfate, and salicylate. If the anion is monovalent (has a charge of $-1$), $A^-$ represents the anion group, if the anion is divalent (has a charge of $-2$), $A^-$ represents half of the anion group, if the anion is trivalent (has a charge of $-3$), $A^-$ represents a third of the anion group, and so on. As will be appreciated given these definitions, m will always equal n in structural formula (1).

The compounds of structural formula (1) include structures that incorporate a piperazine ring. For example, if R* is a —$CH_2CH_2$— group, $Q^1$ and $Q^3$ together or $Q^1$ and $Q^2$ together may be a —$CH_2CH_2$— group to form a six-membered piperazine ring; or, if R** is a —$CH_2CH_2$— group, $Q^3$ and $Q^3$ together may be a —$CH_2CH_2$— group to form a six-membered piperazine ring.

As used in this application, the term "monoalkoxylated compound" or similar term means a compound of structural formula (1) wherein none of v, w, x, y, and z is greater than 1. Thus, a monoalkoxylated compound does not contain any polymeric chains of alkoxy groups (that is, two or more alkoxy groups attached together) attached directly to a nitrogen atom of a compound of structural formula (1). In contrast, the term "polyalkoxylated compound" or similar term means a compound of structural formula (1) wherein any of v, w, x, y, and z is greater than 1. Thus, a polyalkoxylated compound contains at least one polymeric chain of alkoxy groups (that is, two or more alkoxy groups attached together) attached directly to a nitrogen atom of a compound of structural formula (1).

The instant invention involves compounds of structural formula (1) and formulations thereof, and uses thereof. In certain parts of this application, however, distinctions will be made between monoalkoxylated compounds of structural formula (1) and polyalkoxylated compounds of structural formula (1) and such distinctions will be explicitly made. If no such distinction is made, it is be understood that the statement applies both the monoalkoxylated compounds of structural formula (1) and the polyalkoxylated compounds of structural formula (1). Thus, the term "alkoxylated compounds" includes both monoethoxylated compounds and polyethoxylated compounds as defined above. Similarly, the term "ethoxylated compounds" includes both monoethoxylated compounds and polyethoxylated compounds.

The compounds of structural formula (1) can be used alone or in mixtures, used in combination with other compounds or additives, or used as a formulation with other compounds or additives, depending on the intended use and the advantages and disadvantages attendant with each alternative application method. Some examples of compounds or additives that may be used in conjunction with compounds of structural formula (1) or made into formulations with compounds of structural formula (1) include surfactants or detergents, especially quaternary ammonium compounds, perfumes, preservatives, insect and moth repelling agents, polymeric soil release agents, antistatic agents, dyes and colorants, viscosity control agents, antioxidants, silicones, mineral oils and petrolatums, synthetic lubricants, defoaming agents, antifoaming agents, emulsifiers, brighteners, opacifiers, freeze-thaw control agents, shrinkage control agents, and mixtures thereof. Many examples of these additives are set forth in detail and are intended to demonstrate the scope of the invention. Other compounds or additives familiar to those of skill in the art and appropriate to a particular use, however, may also be used with or formulated with the compounds of structural formula (1).

The compounds of structural formula (1) (either alone or in combination with other compounds) have many potential applications. For example, the compounds of structural formula (1) may be used as detailed herein, without limitation, as a fabric softener (either alone or in a combination detergent/fabric softener), as a car spray microemulsion, as a paper debonder, as a hair or skin conditioner, as a corrosion inhibitor, as an asphalt emulsifier, as an organoclay ingredient, or as an agricultural product emulsifier. The polyethoxylated compounds may also find uses as textile treatments, particularly when used in conjunction with a resin bath.

B. APPLICATIONS

The present disclosure shows that the compounds and formulations of the present invention may be used for many purposes and suitable additives may be incorporated therein based on the ultimate application. Such ingredients, for example, may contribute significantly to the ease of formulation, stability, dispersibility, fluidity, and the performance properties of the compositions.

In one aspect, the present invention provides compounds and formulations that have the ability to impart to fabric (that is, articles of clothing, textiles, and so forth), properties including softness to the touch, ease of handling, increased lubricity, and a reduced tendency to carry or pick up static electricity. One form in the compounds and formulations of the present invention are provided is as a liquid, for instance, as an emulsion or as a solution/suspension of the desired components. During use, an appropriate controlled amount of the liquid formulation is employed, for example, by pouring the formulation directly into the washing machine. Typically, the formulation is dispensed during the rinse cycle of the washing machine, either poured in by hand or metered in by an appropriate automatic metering device with which the washing machine is equipped.

In addition, the present invention also provides compounds and formulations that may find use as textile treatments to add lubricity and finishing to the fabric prior to shipping the textile to market, particularly when used in conjunction with a resin bath. In such an application, the textile mill would typically apply the formulation in dilute emulsions and rapidly dry the excess water from the fabric to lubricate the fibers and give it a surface finish.

Moreover, the present invention provides compounds and formulations that have the ability to impart to paper and paper products softness, lubricity, and antistatic properties, and improve ease of handling of the substrate and surface appearance; in the papermaking process, such compounds of the present invention are termed debonders. Debonders are usually added to the paper fibers in the head tank or headbox of a papermaking machine where the paper fibers are pulped as an aqueous slurry just prior to feeding the resulting slurry onto the papermaking or dewatering screen. These debonders condition the fibers to give improved softness feeling to the paper fibers that is valuable for their use in tissue and towel making. The compositions and formulations of the present invention can also be incorporated into the paper or tissue by any suitable means such as spraying or printing onto the surface of the paper or tissue.

The present invention also provides compounds and formulations that are useful in personal care products such as hair or skin conditioners. In this application, the present invention provides formulations that impart softness, lubricity, and improve the surface appearance of the skin or hair. The hair conditioners additionally reduce the tendency for tangling, improve the manageability, and impart a soft feel to the hair strands. Such hair conditioners are applied as dilute emulsions to the hair following its wash or may be incorporated into a combined conditioner and shampoo composition, also known as a conditioning shampoo, two-in-one shampoo, or two-in-one. Such hair and skin conditioning formulations typically incorporate effective amounts, for example, 0.1 wt. % to 10 wt. % or more, of emollients, humectants, and/or slip and conditioning agents, such as organopolysiloxanes and the like, to create formulations that are monophasic and can be made to be translucent or even clear. Compounds suitable for use as emollients, humectants and conditioners in formulations for skin care or hair care can be found in the CTFA Cosmetic Ingredient Dictionary, 3d Edition, and in the CTFA Cosmetic Ingredient Handbook, which are hereby incorporated by reference in their entireties.

The compositions of the present invention are particularly useful in applications that take advantage of their ability to disperse hydrophobic material, to stabilize foam, and to enhance the penetration and wetting exhibited by the compositions. Examples of such compositions and applications are set forth below, each revealing an additional aspect of the present invention.

The compounds and formulations of the present invention may be used as oil dispersants and oil slick dispersant formulations for application onto oil, for example, onto a film of oil, to disperse the oil.

The compounds and formulations of the present invention may also be used as oil well stimulation and oil recovery aids for injection into oil wells in order to penetrate into the surface of the borehole and assist liberation of crude oil from the matrix material into the borehole, from which it can be brought to the surface.

In addition, the compounds and formulations of the present invention may be used as vehicles for hydrophobic sheeting agents such as mineral oil and silicone oil. Such oils can readily be dispersed in compositions, according to the present invention, and the resulting formulations are highly satisfactory when sprayed or otherwise applied to a surface, such as a freshly washed automobile surface, to impart a lustrous, water-repellent film to the surface.

The compounds and formulations of the present invention may also be used as rinse aids, such as used in automatic dishwashers, wherein application of the composition of the present invention disperses residual hydrophobic matter, including cleaner residues and films.

Furthermore, the compounds and formulations of the present invention may be used as paper deinking and ink flotation agents for treating waste inked paper by addition to the pulp slurry such that the ink is liberated from the paper and prevented from redepositing onto the paper. In this application, the ink is typically dispersed or even fully solubilized in the resulting solution when the ink particles are floated from the fibers.

The compounds and formulations of the present invention may also be used as asphalt emulsion agents for emulsifying finely divided asphalt (at loadings of typically 1–20 wt. %), with or without particulate filler such as sand, in an aqueous phase which comprises the composition according to the present invention.

Moreover, the compounds and formulations of the present invention may be used as corrosion inhibitor agents for application to any surface to which one desires to apply a film that protects against corrosion. The composition would typically contain an effective amount of a hydrophobic corrosion inhibiting material, such as liquid or waxy-solid fatty ester, paraffinic hydrocarbon, silicone, or the like, dispersed in a composition according to the present invention.

In addition, the compounds and formulations of the present invention may be used with ore flotation agents for separating ore from rock. Such floatation agents might include, for example, the agent available from Witco Corporation under the tradename WITCAMINE® AL42-12. Typically, the ore floatation agent (a collector or frother, depending on the characteristics of the particular separation desired in the flotation cell) or mixture thereof, which is a relatively hydrophobic material, is dispersed in a composition according to the invention and an effective amount is added (on a batch or continuous basis) to the ore separation cell. This permits the formulator to improve the dispersibility of the hydrophobic ore floatation agent, which often improves the performance of the mineral separation by improving the efficiency of the floatation agent's dispersibility. This can enable the operator to use smaller amounts of the ore floatation agent to achieve the desired purpose because there is a higher concentration of active ingredients available.

In addition, the compounds and formulations of the present invention may be used as suspension concentrates and emulsifiable concentrates of herbicides, pesticides, miticides, fungicides, or bactericides, wherein one or more liquid or solid, generally hydrophobic, active ingredients are dispersed in a composition according to the present invention. The resulting concentrate can be applied as a concentrate on or around desired vegetation, but is more often mixed with water (for example, at the point of use) to form a final dilute formulation having the desired concentration of active ingredient(s). This application takes advantage of the noteworthy property of this invention that addition of the water does not disrupt the monophasic state, nor the fluidity, of the formulation.

As noted above, the compositions and formulations of the present invention can also optionally contain other components, depending on the additional properties one may wish to provide in the finished composition. Such additional components include, but are not limited to, additional coupling agents and solvents, additional quaternary ammonium compounds, additional surfactants, hydrocarbon actives, perfumes, preservatives including bacteriocides and fungicides, insect and moth repelling agents, polymeric soil release agents, antistatic agents, dyes and colorants, especially bluing agents, viscosity control agents, antioxidants, silicones, defoaming agents, antifoaming agents, emulsifiers, brighteners, opacifiers, freeze-thaw control agents, shrinkage control agents, aloe, humectants, skin protectants, feel modifiers, and mixtures thereof.

C. SYNTHESIS

Compounds of structural formula (1) can easily be synthesized from readily available starting materials using reaction procedures and conditions quite familiar to those of ordinary skill in this art. The preferred procedure begins with a diamine, triamine or tetramine of structural formula $H_2N$—$R^*$—$(NH$—$R^{**})_r$—$NH_2$. Preferred compounds having the required structural formula include hexamethylenediamine (HMDA); bis(hexamethylene)triamine (BHMT); 1,2-diaminocyclohexane, available from DuPont Chemical Co. under the tradename DCH-99; 1,3-pentanediamine available from DuPont Chemical Co. under the tradename DYTEK™ diamine; and 2-methylpentamethylenediamine (MPMD) available from DuPont Chemical Co. under the tradename DYTEK™ A diamine. This polyamine compound is next alkoxylated using an alkoxylating agent. The alkoxylating agents may be ethylene oxide (EO), propylene oxide (PO), isopropylene oxide (iPO), or butylene oxide (BO), or (less preferred) a mixture thereof, depending on the desired choice of alkyl groups to become attached to the respective nitrogen atoms. The number of moles of alkylene oxide reactant and the reaction conditions are established such that the terminal primary amine hydrogen atoms are disubstituted with hydroxyalkyl, and each of the secondary amines, if any, is monosubstituted with hydroxyalkyl. It should be noted that polyethoxylated polyamine products typically are quite dark (4–8 Gardner units) after only 8 to 12 moles of EO are added. If colorless polyalkoxylated products are desired, it is often necessary to react the polyamine with a sufficient amount of PO, iPO, or BO or a mixture thereof to convert the amine groups into tertiary amine groups before addition of EO, usually with the addition of sodium borohydride and an alkaline catalyst. Although such product is not a pure ethoxylated amine, it is desirably colorless.

Next, the alkoxylated product is esterified by reaction of fatty acids with the respective hydroxyl groups resulting from the alkoxylation. As indicated above, the molecule may be completely esterified, but it is preferred for formulation reasons to achieve only partial esterification. There should, however, be at least one ester group per molecule of structural formula (1).

The esterification is carried out with carboxylic acids of structural formula $R^A C(O)OH$, wherein $R^A$ is straight or branched alkyl or alkenyl containing 9 to 21 carbon atoms and 0 to 4 carbon-carbon double bonds. While the esterification can be carried out with an appropriate quantity of one such carboxylic acid, it is preferred for reasons of economy, product performance, and convenience to employ mixtures of carboxylic acids each corresponding to structural formula $R^A C(O)OH$. For instance, mixtures of such fatty acids from various animal and vegetable origins are conveniently commercially available. One example of such material is tallow fatty acids which, as is generally known in this field, is a mixture of fatty acids predominantly composed of fatty acids containing 14, 16, and 18 carbon atoms, and 0, 1, and 2 degrees of unsaturation. Other preferred sources include coconut fatty acids and canola fatty acids, although any suitable fatty acid may be used. Esterification is carried out under conventional conditions, well-known to the chemist in this field, allowing for the withdrawal of byproduct water. The number of moles of fatty acid is selected to provide the desired average degree of esterification in the mixture of products formed upon esterification.

Next, if desired, the esterified product or mixture of esterified products is quaternized and/or protonated. As recognized hereinabove, the esterified product can be completely quaternized, but it is preferred to carry out partial quaternization only, if any. Quaternization is carried out under conditions well known in this field for quaternization of amines, by reaction of the esterified amine with a suitable quaternizing agent. The quaternizing agents have the formulas $Q^1A$ and $Q^2A$, which can of course be the same and preferably are the same. With triamines and tetramines a second (or third) quaternizing agent $Q^3A$ can be used; it is likewise preferably the same as $Q^1A$ and $Q^2A$. Preferably, only one particular quaternizing agent is employed, in which case all of the quaternizing substituents Q will be the same. Preferred quaternizing agents include methyl chloride, dimethyl sulfate (DMS), and diethyl sulfate (DES).

Protonation, if desired, can be carried out by reacting the esterified product or mixture of products with an acid of the formula HA, such as hydrochloric acid, or other strong acids, such as sulfuric acid or phosphoric acid.

Each of the foregoing reactions can be carried out in solvent or in solvent-free conditions, in each case employing conditions well established for the respective reactions in this field.

Preferred diamine compounds of the present invention include hexamethylenediamine (HMDA) alkoxylated ester diamines or quats, most preferably HMDA alkoxylated ester quats, which are made according to the above method. Accordingly, HMDA may be reacted with 4 moles of alkoxylating agent per mole of HMDA. If a polyalkoxylated HMDA ester compound is desired, more than 4 moles of alkoxylating agent would be used, for example, 4.1 to 32 moles of ethylene oxide. The resulting HMDA alkoxylate is then esterified by reaction with 1 to 4 moles of fatty acid, for example, tallow fatty acid. The resulting HMDA alkoxylated ester may then be quaternized with up to 2 moles of dimethyl sulfate (DMS) per mole of HMDA. Example 1 below details the synthesis of a particular HMDA monoalkoxylated ester quat.

Preferred triamine compounds of the present invention include bis(hexamethylene)triamine (BHIMT) alkoxylated ester quats, most preferably BHMT ethoxylated ester quats, which are made according to the above method. Accordingly, BHMT may be reacted with 5 moles of ethylene oxide per mole of BHMT. If a polyalkoxylated BHMT ester compound is desired, more than 5 moles of alkoxylating agent would be used, for example, 5.1 to 40 moles of ethylene oxide. The resulting BHMT alkoxylate is then esterified by reaction with 5 moles of fatty acid, for example, canola fatty acid. The resulting BHMT alkoxylated ester may then be quaternized with up to 3 moles of dimethyl sulfate (DMS) per mole of BHMT.

D. FORMULATIONS AND PROPERTIES

The products as described herein exhibit a number of desirable properties making them particularly suitable for formulation into commercial products such as fabric softeners and other commercial products, as mentioned above.

Most notably, the compounds of structural formula (1) can readily be formulated into useful compositions such as aqueous compositions, which achieve the desired functionality and which are clear, that is, transparent or translucent. This property can be realized at a variety of concentrations of active ingredient, with or even without special solvents or coupling agents. In addition, microemulsion formulations can be made that improve the ease of application and effectiveness of the resulting formulation.

Emulsion or microemulsion formulations according to the present invention have many applications, for example, as car "cheater" wax spray technology to improve beading and act as a drying aid, as fabric softeners, and as personal care products, for example, as a moisturizer/conditioner if the compound of structural formula (1) is not skin irritating. In addition, such emulsions or microemulsions may find uses in paper debonding/finishing, as emulsifiers for silicone oils and pesticides, and as emulsifiers/softeners for textile finishing. Generally such formulations include three components: (a) compound of structural formula (1), (b) a solvatrope or coupling agent and blends thereof, and (c) an oil or hydrophobic organic component and blends thereof, which are blended in water. These microemulsion formulations give stable, clear (translucent) products that do not go through thick or viscous gel phases but disperse readily and quickly into very fine particle size microemulsions when diluted or dispersed in water. These microemulsions have many additional advantages over conventional microemulsions, such as the products sold by Witco Corporation under the tradename CARSPRAY™: reduced particle size, improved beading and sheeting over, and improved biodegradability, especially when used with methyl ester oils.

If the resulting formulation is intended to be used as a personal care formulation, the amount of the compound of structural formula (1) is about 0.1 wt. % to about 65 wt. % of the formulation, preferably about 0.1 wt. % to about 25 wt. %, and most preferably about 0.1 wt. % to about 5 wt. %; the amount of solvatrope or coupling agent is about 0.1 wt. % to about 65 wt. % of the formulation, preferably about 0.1 wt. % about 25 wt. %, and most preferably about 0.1 wt. % to about 0.5 wt. %; the amount of oil or hydrophobic organic component is about 0.1 wt. % to 65 wt. % of the formulation, preferably about 0.1 wt. % to about 25 wt. %, and most preferably about 0.1 wt. % to about 5 wt. %; and the amount of water is about 20 to 99.7 wt. % of the formulation, preferably about 35 wt. % to about 99.7 wt. %, and most preferably about 65 wt. % to about 99.7 wt. %. A further example of personal care microemulsions according to the invention is provided below as Example 29.

If the resulting formulation is intended to be used in a car drying aid formulation or other application, the amount of the compound of structural formula (1) is about 5 wt. % to about 50 wt. % of the formulation, preferably about 10 wt. % to about 30 wt. %, and most preferably about 15 wt. % to about 25 wt. %; the amount of solvatrope or coupling agent is about 2 wt. % to about 15 wt. % of the formulation, preferably about 3 wt. % to about 10 wt. %, and most preferably about 6 wt. % to about 10 wt. %; the amount of oil or hydrophobic organic component is about 5 wt. % to 50 wt. % of the formulation, preferably about 10 wt. % to about 30 wt. %, and most preferably about 15 wt. % to about 20 wt. %; and the amount of water is about 10 to 70 wt. % of the formulation, preferably about 20 wt. % to about 60 wt. %, and most preferably about 30 wt. % to about 50 wt. %.

Other properties are realized as well. For instance, as noted above, the products are biodegradable. Surprisingly, the embodiments which have no Q substituents, or wherein the only Q substituents are —H, exhibit particularly high biodegradability. Also, the compounds of structural formula (1) exhibit advantageous stability, solubility, and freedom from excessively objectionable color and odor.

The color and odor stability is exhibited in formulations wherein the compound or compounds of structural formula (1) are the only nitrogenous compounds present. Color and order stability is also exhibited in formulations wherein one or more compounds of structural formula (1) is present with one or more additional conventional quaternary ammonium compounds. Thus, the compounds of the present invention improve the color and odor stability of the other conventional quaternary ammonium compounds present.

The color stability property is shown in the following data, in which color stability was assessed by heating samples of each product shown in Table I to 110° C. in open tubes in an air circulation oven, periodically measuring the color in Gardner units and calculating the color change over time:

TABLE I

| | Color (Gardner units) | | | | Rate of color change (Gardner units)/day | |
|---|---|---|---|---|---|---|
| Product | start | 1 day | 2 days | 6 days | At 2 days | At 6 days |
| 1 | 2.5 | 4.5 | 6.0 | 14.5 | 1.75 | 2.0 |
| 2 | 1 | 4.5 | 6.5 | 16 | 2.75 | 2.5 |
| 3 | 1 | 1.5 | 4 | 8.5 | 1.5 | 1.3 |
| 4 | 4 | — | — | 11.5* | — | 1.9* |
| 5 | 2.5 | 5.5 | 6.5 | 12.5 | 2.0 | 1.7 |
| 6 | 3 | 4.5 | 5.5 | 5.5 | 1.25 | 0.4 |
| 7 | 2.5 | 3.5 | 3.5 | 3.5 | 0.5 | 0.17 |
| 8 | 1 | 1 | 2 | 3.5 | 0.5 | 0.4 |
| 9 | 2.5 | 2.5 | 2.5 | 2.5 | 0 | 0 |
| 10 | 1.5 | 1.5 | 1.5 | 1.5 | 0 | 0 |
| 11 | 1.5 | 1.5 | 1.5 | 2.5 | 0 | 0.17 |
| 12 | 2.5 | 5.5 | 7.5 | 11.5 | 2.5 | 1.5 |
| 13 | 1 | — | — | 3.5* | — | 0.62* |
| 14 | 1.5 | — | — | 5.5* | — | 1.0* |

*denotes 4 day readings and averages
Key to product numbers:
1: Soft tallow-derived, triethanolamine-ester quaternary
2: Soft tallow-derived, methyl diethanolamine-ester quaternary
3: Canola-derived, triethanolamine-ester quaternary
4: Soft tallow-derived, diamidoamine quaternary
5: HMDA + 4 moles ethylene oxide + 2.5 moles soft tallow fatty acids + 1 mole DMS
6: Same as 5 except 2 moles DMS used
7: Same as 6 except 2 moles of canola fatty acid used
8: BHMT + 5 moles ethylene oxide + 4 moles soft tallow fatty acid + 3 moles DMS
9: Same as 8 except 1 mole soft tallow fatty acid used
10: Same as 8 except 2 moles soft tallow fatty acid used
11: Same as 8 except 3 moles canola fatty acid used
12: Same as 8 except 2 moles soft tallow fatty acid used and product not quaternized
13: 50/50 (wt. %) mixture of 1 and 8
14: 50/50 (wt. %) mixture of 1 and BHMT + 5 moles ethylene oxide + 3.5 moles soft tallow fatty acid + 3 moles DMS Although the compounds of structural formula (1) have many potential uses, in particular, they exhibit highly satisfactory fabric softening capabilities. Thus, the compounds of structural formula (1), as well as mixtures of such compounds, can be advantageously formulated appropriately into products useable as fabric softeners. It has been found that, regardless of the other components that may be present in the fabric softener formulation, the pH of the formulation as a whole should be below 5, and preferably 2.5 to 4.0, in order to maintain low susceptibility of the ester functionality to hydrolysis in water. The preferred method for providing or adjusting the desired pH value is adding small amounts of an acid, such as HCl or $H_2SO_4$, consistent with appropriate adjustment of the average degree of esterification and average degree of quaternization mixture of compounds corresponding to structural formula (1). Preferred emulsions useful as fabric softener compositions can contain about 2 wt. % to about 80 wt. %, preferably 5 wt. % to 30 wt. %, and more preferably 6 wt. % to 25 wt. %, of one or more compounds corresponding to structural formula (1). In general, higher solids contents can be provided more easily with lower degrees of quaternization. On the other hand, higher degrees of quaternization (such as a degree of quaternization approaching 2.0 for a diamine), lead to aqueous formulations wherein the maximum acceptable solids content without excessive solubility problems is lower.

The compounds of structural formula (1) can be formulated into compositions, including clear fabric softener compositions. Such fabric softening composition would typically include water and one or more of the solvents which are conventionally used in formulating fabric softeners. Examples of such solvents include ethanol, isopropanol, hexylene glycol, propylene glycol, diethylene glycol, or similar solvent of mixture thereof, as a concentrate or more dilute form, depending on the application. Selection of a suitable solvent for a particular application is well-known to those of skill in the art. Such formulations generally comprise about 10 wt. % up to about 50 wt. % of one compound of structural formula (1) or a mixture thereof.

The compounds of structural formula (1) can be formulated with greater ease than is encountered with conventional quaternary ammonium fabric softener actives. Most conventional quaternary ammonium compounds exhibit a tendency to form a gel during dilution with water when formulated in clear formulations. When formulated in clear formulations, however, the compounds of structural formula (1) show very little gelation, or no gelation at all, during dilution with water, even cold water, which would be expected to provoke gelation. This freedom from a tendency to gel means that compositions including compounds of structural formula (1) can be prepared at active concentrations of 40 wt. % or higher, for example, even 50 wt. % or higher. The preparation itself of such formulations is much simpler: the freedom from gelation means that when a formulator chooses to manufacture a more concentrated product for resale to the consumer, there is no need for special treatment to deal with gel formation. Also, the freedom from gel formation means that the consumer can use the more concentrated product directly without concern that a gelled byproduct would form. For example, the consumer could add a concentrated fabric softener composition according to the present invention directly into the wash water in the wash or rinse cycle, without any apprehension that a gel will form that that would reduce softening efficiency or leave a deposit on the clothes.

It should be noted that the ability of the compounds of structural formula (1) to form a clear formulation, at lower and at higher concentrations, extends also to formulations which also contain one or more other quaternary ammonium compounds as fabric softener co-actives, as well as other additives as disclosed herein.

E. ADDITIONAL QUATERNARY AMMONIUM COMPOUNDS

Additional conventional quaternary ammonium compounds or salts may be present with the compound or compounds of structural formula (1) in accordance with the present invention. The compounds presented below are only examples of conventional quaternary compounds that are suitable for use in the formulations of the present invention. As with the compounds of structural formula (1), these conventional quaternary ammonium compounds (quats or salts) may have an anion to provide electrical neutrality and, in general, such anion may be any anion which is not deleterious to the properties of the overall compound. Thus, in the structural formulas (i) to (xxii) below, the counter anion, whether designated as $A^-$ or not shown but understood, may be selected, without limitation, from the group consisting of fluoride, chloride, bromide, iodide, chlorite, chlorate, hydroxide, hypophosphite, phosphite, phosphate, carbonate, formate, acetate, lactate, and other carboxylates, oxalate, methyl sulfate, ethyl sulfate, benzoate, and salicylate, and the like. Preferred examples of the anions are chloride, bromide, methyl sulfate, ethyl sulfate, and salicylate. If the anion is monovalent (has a charge of $-1$), $A^-$ represents the anion group, if the anion is divalent (has a charge of $-2$), $A^-$ represents half of the anion group, if the anion is trivalent (has a charge of $-3$), $A^-$ represents a third of the anion group, and so on.

The conventional quats that may be formulated with the compounds of structural formula (1) in accordance with the present invention include, but are not limited to, nitrogenous compounds selected from the group consisting of quaternized or acid salt derivatives of:

(i) alkylenediamines, including compounds of the formula:

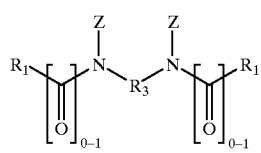

wherein each $R_1$ is an acyclic alkyl or alkylene $C_{12}-C_{21}$ hydrocarbon group, each Z is $-(R_2O)_{0-4}H$, or $-R_2H$, and $R_2$ and $R_3$ are divalent $C_1-C_6$ alkylene groups;

(ii) substituted imidazoline compounds having the formula:

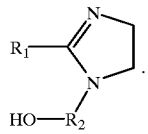

(iii) reaction products of higher fatty acids with alkylenetriamines in, for example, a molecular ratio of about 2:1, the reaction products containing compounds of the formula:

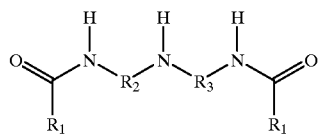

wherein $R_1$, $R_2$ and $R_3$ are defined as above; and (iv) substituted imidazoline compounds having the formula:

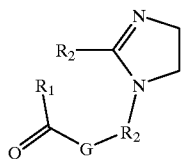

wherein G is —O— or —NH— and $R_1$ and $R_2$ are defined as above; and mixtures thereof.

Preferred examples of compounds of structural formula (i) are those derived from hydrogenated tallow fatty acids and the hydroxyalkylalkylenediamine is N-2-hydroxyethylethylenediamine, such that $R_1$ is an aliphatic $C_{15}$–$C_2$, hydrocarbon group, and $R_2$ and $R_3$ are divalent ethylene groups.

A preferred example of a compound of structural formula (iii) is stearic hydroxyethyl imidazoline, wherein $R_1$ is an aliphatic $C_{21}$ hydrocarbon group and $R_2$ is a divalent ethylene group.

A preferred example of compounds of structural formula (iii) is N,N"-ditallowalkanoyldiethylenetriamine where $R_1$ is an aliphatic $C_{15}$–$C_{21}$ hydrocarbon group and $R_2$ and $R_3$ are divalent ethylene groups.

A preferred example of compounds of structural formula (iv) is 1-tallowamidoethyl-2-tallowimidazoline wherein $R_1$ is an aliphatic $C_{15}$–$C_{21}$ hydrocarbon group and $R_2$ is a divalent ethylene group.

Both N,N"-ditallowalkanoyldiethylenetriamine and 1-tallowethylamido-2-tallowimidazoline are reaction products of tallow fatty acids and diethylenetriamine, and are precursors of the cationic fabric softening agent methyl-1-tallowamidoethyl-2-tallowimidazolinium methylsulfate (see "Cationic Surface Active Agents as Fabric Softeners," R. R. Egan, *Journal of the American Oil & Chemicals Society*, January 1978, pages 118–121). N,N"-ditallowalkanoyldiethylenetriamine and 1-tallowamidoethyl-2-tallowimidazoline can be obtained from Witco Corporation. Methyl-1-tallowamidoethyl-2-tallowimidazolinium methylsulfate is available from Witco Corporation under the tradename VARISOFT® 475.

Other suitable quats are those containing one long chain acyclic aliphatic $C_8$–$C_{22}$ hydrocarbon group, selected from the group consisting of:

(v) acyclic quaternary ammonium salts having the formula:

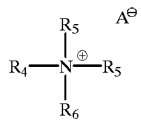

wherein $R_4$ is an acyclic aliphatic $C_8$–$C_{22}$ hydrocarbon group, alkyl, benzyl or $(C_4$–$C_{18}$ alkyl)—$(OCH_2CH_2)_{2-3}$—, $R_5$ and $R_6$ are $C_1$–$C_4$ saturated alkyl or hydroxyalkyl groups, and $A^-$ is an anion as defined above;

(vi) substituted imidazolinium salts having the formula:

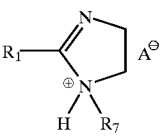

wherein $R_1$ is an acyclic alkyl or alkylene $C_{12}$–$C_{21}$ hydrocarbon group, $R_7$ is hydrogen or a $C_1$–$C_4$ saturated alkyl or hydroxyalkyl group, and $A^-$ is an anion as defined above;

(vii) substituted inidazolinium salts having the formula:

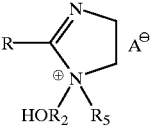

wherein $R_1$, $R_2$, $R_5$, and $A^-$ are as defined above;
(viii) alkylpyridinium salts having the formula:

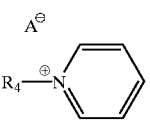

wherein $R_4$ is an acyclic aliphatic $C_8$–$C_{22}$ hydrocarbon group and $A^-$ is an anion as defined above; and
(ix) alkanamide alkylene pyridinium salts having the formula:

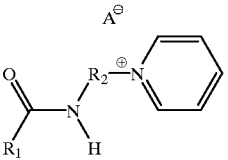

wherein $R_1$ is an acyclic aliphatic $C_{12}$–$C_{21}$ hydrocarbon group, $R_2$ is a divalent $C_1$–$C_6$ alkylene group, and $A^-$ is an anion as defined above; and mixtures thereof.

Examples of compounds of structural formula (v) are the monoalkyltrimethylammonium salts such as monotallowtrimethylammonium chloride, mono(hydrogenated tallow)-trimethylammonium chloride, palmityltrirnethylammonium chloride and soyatrimethylammonium chloride, available from Witco Corporation under the tradenames ADOGEN® 471, ADOGEN® 441, ADOGEN® 444, and ADOGEN® 415, respectively. In these compounds, $R_4$ is an acyclic aliphatic $C_{16}$–$C_{18}$ hydrocarbon group, and $R_5$ and $R_6$ are methyl groups. Mono(hydrogenated tallow) trimethylammonium chloride and monotallowtrimethylammonium chloride are preferred. Other examples of compounds of structural formula (v) are behenyltrimethylammonium chloride wherein $R_4$ is a $C_{22}$ hydrocarbon group, which is available from the Humko Chemical Division of Witco Corporation under the tradename KEMAMINE® Q2803-C; soyadimethylethylammonium ethylsulfate wherein $R_4$ is a $C_{16}$–$C_{18}$ hydrocarbon group, $R_5$ is a methyl group, $R_6$ is an ethyl group, and $A^-$ is an ethylsulfate anion; and methyl bis(2-hydroxyethyl)

octadecylammonium chloride wherein $R_4$ is a $C_{18}$ hydrocarbon group, $R_5$ is a 2-hydroxyethyl group and $R_6$ is a methyl group.

An example of a compound of structural formula (vii) is 1-ethyl-1-(2-hydroxyethyl)-2-isoheptadecylimidazolinium ethylsulfate wherein $R_1$ is a $C_{17}$ hydrocarbon group, $R_2$ is an ethylene group, $R_5$ is an ethyl group, and $A^-$ is an ethylsulfate anion.

Other quats useful in the present invention include cationic nitrogenous salts having two or more long chain acyclic aliphatic $C_8$–$C_{22}$ hydrocarbon groups or one long chain acyclic aliphatic $C_8$–$C_{22}$ hydrocarbon group and an arylalkyl group.

Examples include:

(x) acyclic quaternary ammonium salts having the formula:

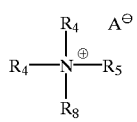

wherein each $R_4$ is an acyclic aliphatic $C_8$–$C_{22}$ hydrocarbon group, $R_5$ is a $C_1$–$C_4$ saturated alkyl or hydroxyalkyl group, $R_8$ is selected from the group consisting of $R_4$ and $R_5$ groups, and $A^-$ is an anion as defined above;

(xi) diamido quaternary ammonium salts having the formula:

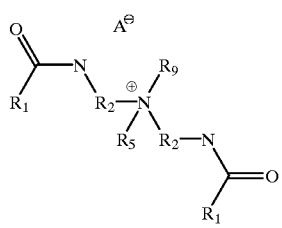

wherein each $R_1$ is an acyclic alkyl or alkylene $C_{12}$–$C_{21}$ hydrocarbon group, each $R_2$ is a divalent alkylene group having 1 to 3 carbon atoms, $R_5$ and $R_9$ are $C_1$–$C_4$ saturated alkyl or hydroxyalkyl groups, and $A^-$ is an anion as defined above;

(xii) alkoxylated diamido quaternary ammonium salts having the formula:

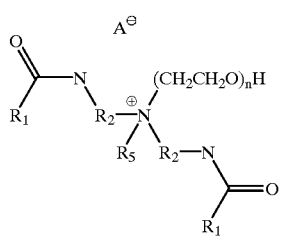

wherein n is equal to 1 to about 5, and $R_1$, $R_2$, $R_5$, and $A^-$ are as defined above;

(xiii) quaternary ammonium compounds having the formula:

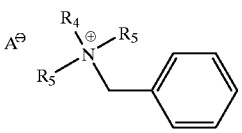

wherein $R_4$ is an acyclic aliphatic $C_8$–$C_{22}$ hydrocarbon group, each $R_5$ is a $C_1$–$C_4$ saturated alkyl or hydroxyalkyl group, and $A^-$ is an anion as defined above;

(xiv) amide-substituted imidazolinium salts having the formula:

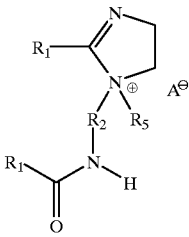

wherein each $R_1$ is an acyclic aliphatic $C_{12}$–$C_{21}$ hydrocarbon group, $R_2$ is a divalent alkylene group having 1 to 3 carbon atoms, and $R_5$ and $A^-$ are as defined above, or $R_5$ is —H; and (xv) ester-substituted imidazolinium salts having the formula:

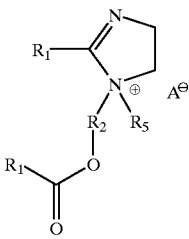

wherein $R_1$, $R_2$, $R_5$, and $A^-$ are as defined above; and mixtures thereof.

Examples of compounds of structural formula (x) are the well-known dialkyldimethylammonium salts such as ditallowdimethylammonium chloride, ditallowdimethylammonium methylsulfate, di(hydrogenated tallow) dimethylammonium chloride, distearyldimethylammonium chloride, dibehenyldimethylammonium chloride. Di(hydrogenated tallow)dimethylammonium chloride and ditallowdimethylammonium chloride are preferred. Examples of commercially available dialkyldimethylammonium salts usable in the present invention are di(hydrogenated tallow)dimethylammonium chloride (available from Witco Corporation under the tradename ADOGEN® 442); ditallowdimethylammonium chloride (available from Witco Corporation under the tradename ADOGEN® 470); distearyldimethylammonium chloride (available from Witco Corporation under the tradename AROSURF® TA-100); dicocodimethyl ammonium chloride (available from Witco Corporation under the tradename ADOGEN® 462), and dibehenyldimethylammonium chloride, wherein $R_4$ is an acyclic aliphatic $C_{22}$ hydrocarbon group (available from the Humko Chemical Division of Witco Corporation under the tradename KEMAMINE® Q-2802C).

Examples of compounds of structural formula (xi) are methylbis(tallowamidoethyl)(2-hydroxyethyl)ammonium methylsulfate and methylbis(hydrogenated tallowamidoethyl)(2-hydroxyethyl)ammonium methylsulfate, wherein $R_1$ is an acyclic aliphatic $C_{15}$–$C_{17}$ hydrocarbon group, $R_2$ is an ethylene group, $R_5$ is a methyl group, $R_9$ is a hydroxyalkyl group and $A^-$ is a methylsulfate anion; both of these materials are available from Witco Corporation under the tradenames VARISOFT® 222 and VARISOFT® 110, respectively.

An example of a compound of structural formula (xiii) is dimethylstearylbenzylan-unonium chloride, wherein $R_4$ is an acyclic aliphatic $C_{18}$ hydrocarbon group, $R_5$ is a methyl group and $A^-$ is chloride, which is available from Witco Corporation under the tradename VARISOFT® SDC.

Examples of compounds of structural formula (xiv) are 1-methyl-1-tallowamidoethyl-2-tallowimidazolinium methylsulfate and 1-methyl-1-(hydrogenated tallowamidoethyl)-2-(hydrogenated tallow)imidazolinium methylsulfate wherein $R_1$ is an acyclic aliphatic $C_{15}$–$C_{17}$ hydrocarbon group, $R_2$ is an ethylene group, $R_5$ is a methyl group and $A^-$ is a chloride anion; available from Witco Corporation under the tradenames VARISOFT® 475 and VARISOFT® 445, respectively.

Additional examples of quaternary ammonium compounds useful in the present invention include:

(xvi) compounds having the formula:

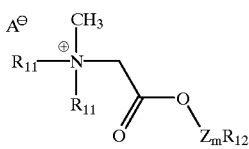

wherein $R_{11}$ is selected from the group consisting of: (a) —$CH_3$, —$CH_2CH_3$, —$CH_2CH_2OH$, or straight chain aliphatic hydrocarbon groups each of which contains from 12 through 24 carbon atoms, (b) ether groups each of which has the structure: $R_{13}O(CH_2O)_y$—, (c) amide groups each of which has the structure:

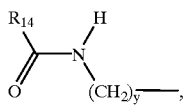

and (d) ester groups each of which has the structure:

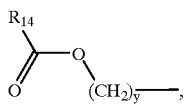

$R_{12}$ is a straight chain aliphatic hydrocarbon group containing from 8 to 32 carbon atoms, $R_{13}$ is a straight chain aliphatic hydrocarbon group containing from 8 to 21 carbon atoms, $R_{14}$ is a straight chain aliphatic hydrocarbon group containing from 7 to 17 carbon atoms, Z is an alkoxy group containing one oxygen atom and either two or three carbon atoms, $A^-$ is an anion as defined above, m is an integer from 1 through 12, and y is an integer which is either 2 or 3.

Yet additional examples of fabric softening compounds useful in the present invention include:

(xvii) compounds having the formula:

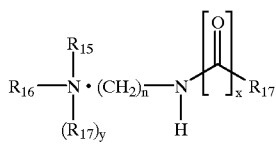

wherein $R_{15}$ is hydrogen or $C_1$–$C_4$ alkyl, each $R_{16}$ is $C_1$–$C_4$ alkyl or

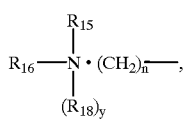

each $R_{17}$ is a $C_8$–$C_{28}$ alkyl or alkenyl group, $R_{18}$ is hydrogen or $C_1$–$C_4$ alkyl, each y is 0 or 1, x is 0 or 1, and each n is from 1 to 6;

(xviii) amides represented by the structural formula:

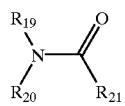

wherein $R_{19}$ and $R_{20}$ are selected independently from the group consisting of $C_{1-22}$ alk(en)yl aryl or alkyl aryl groups, $R_{21}$ is hydrogen or a $C_{1-22}$ alk(en)yl, aryl or alkyl-aryl group or is O—$R_{22}$, wherein $R_{22}$ is a $C_{1-22}$ alk(en)yl, aryl or alkyl-aryl group, and $R_{21}$ and $R_{22}$ optionally contain 1 to 10 alkylene oxide units or functional groups selected from hydroxy, amine, amide, ester, and ether groups; the aryl groups being possibly derived from heterocyclic compounds; at least one of the $R_{19}$ and $R_{20}$ groups contains 10 or more carbon atoms; and where the sum of carbon atoms in $R_{19}+R_{20}+R_{21}$ is equal to or greater than 14. Preferably, the sum of carbon atoms in $R_{19}+R_{20}$ is equal to or greater than 16. Examples of compounds of structural formula (xviii) include N,N-ditallow acetamide, N,N-dicoconut acetamide, N,N-dioctadecyl propanamide, N-dodecyl-N-octadecyl acetamide, N-hexadecyl-N-dodecyl butanamide, N,N-ditallow benzamide, N,N-dicoconut benzamide, and N,N-ditallow 2-phenyl acetamide.

Additional fabric softening compounds useful in the present invention include all ester quaternaries, including but not limited to:

(xix) compounds of the following structural formulas:

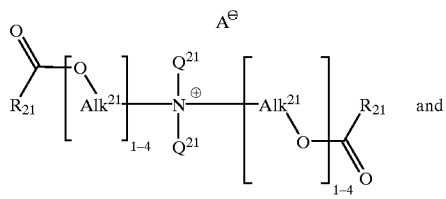

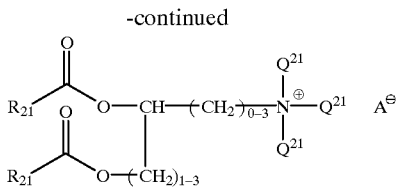

wherein
each $R_{21}$ is independently a saturated or unsaturated alkyl or allylene radical containing 12 to 22 carbon atoms;
each $Q^{21}$ is independently an alkyl group containing 1 to 4 carbon atoms, enzyl, —$CH_2CH_2OH$, —$CH_2CH(OH)CH_3$, or $R_{21}$—C(O)—(O—(Alk$^{21}$))$_{1-4}$—;
each Alk$^{21}$ is independently $C_2H_4$, $C_3H_6$ or $C_4H_8$; and
$A^-$ is an anion as defined above;

(xx) compounds of the formula:

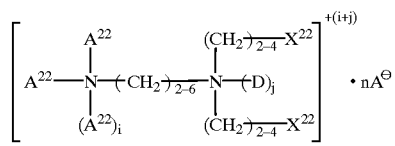

wherein each $A^{22}$ is the same or different and each is alkyl containing up to 3 carbon atoms, benzyl, or H—(Alk$^{22}$—O)$_{13}$—Alk$^{22}$— wherein each Alk$^{22}$ signifies —$CH_2CH_2$—, —$CH(CH_3)CH_2$—, or —$CH_2CH(CH_3)$—, provided further that one of the $A^{22}$ can be hydrogen;

D is methyl, ethyl, propyl, —(CH$_2$)$_{1-3}$COO—, benzyl or hydrogen;

i is 0 or 1 and j is 0 or 1, provided that the sum of (i+j) is 1 or 2;

each $X^{22}$ is a straight or branched saturated or unsaturated aliphatic group containing up to 3 carbon-carbon double bonds and containing 11 to 23 carbon atoms;

n is two minus the number of —(CH$_2$)$_{1-3}$COO— substituents present; and $A^-$ is an anion as defined above;

(xxi) compounds of the formula:

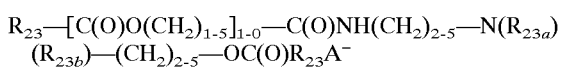

wherein
each $R_{23}$ is independently straight or branched alkyl or alkenyl containing 8 to 22 carbon atoms;
$R_{23a}$ is straight or branched alkyl or hydroxyalkyl containing 1 to 3 carbon atoms, benzyl, or —$C_2H_4OC(O)R_{26}$, wherein $R_{26}$ is straight or branched alkyl or alkenyl containing 8 to 22 carbon atoms;
$R_{23b}$ is —H, —$CH_3$, —$C_2H_5$ or benzyl; and
$A^-$ is an anion as defined above; and (xxii) compounds of the following structural formulas:

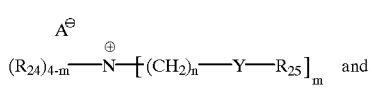

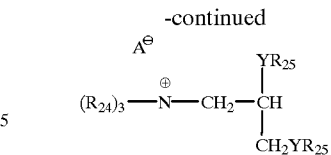

wherein
each $R_{24}$ is independently straight or branched alkyl or alkenyl containing 1 to 8 carbon atoms and 0 to 3 hydroxyl groups;
each $R_{25}$ is straight or branched alkyl or alkenyl containing 10 to 22 carbon atoms and 0 to 3 hydroxyl groups;
each Y is —O—C(O)— or —C(O)—O—;
each m is 1 to 3;
each n is from 1 to 8; and
$A^-$ is an anion as defined above.

Preferred examples of compounds of structural formulas (xxii) include methyl diethanolamine (MDEA) ester quats, triethanolamine (TEA) ester quats, for example, di-(tallow carboxyethyl) hydroxyethyl methylammonium methosulfate, available from Witco Corporation under the tradename REWOQUAT™ WE 16, or epichlorohydrin-based ester quats, all of which are used and accepted as fabric softeners worldwide because of their favorable biodegradation profiles, but usually lack the optimum softening performance of other quats.

F. DIOL AND DIOL ALKOXYLATE COUPLING AGENT ADDITIVES

In a preferred embodiment of this invention, fabric softener formulations and other formulations which may be clear (translucent or transparent) and easily dispersed in water can be provided by including an appropriate amount of one or more straight or branched alkyl diols containing 4 to 12 carbon atoms, and/or alkoxylates of such diols with up to 40 alkoxy units per diol moiety, wherein the alkoxylate chains are composed of alkoxy units which are ethoxy, propoxy or butoxy or mixtures thereof, and preferably ethoxy or isopropoxy. These diol and diol alkoxylate hydrotropes or coupling agents are added to the formulations to increase the amount of the relatively water-insoluble surfactants that can be solubilized into the system. In most cases, they do not act as surfactants to lower surface tension but they often allow surfactants in the presence of salts or electrolytes to be added and subsequently dispersed into water at higher concentrations or at lower viscosities of the formulation than is otherwise achieved using only surfactant and water. These coupling agents assist surfactants by increasing the surfactant's solubility in water and its stability in the formulation, especially in the presence of salts, electrolytes and/or pH agents.

These diols and alkoxylates correspond to structural formula (T)

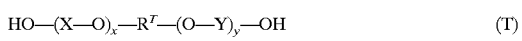

wherein each X and each Y is ethylene (that is, —$C_2H_4$—), propylene (that is, —$C_3H_6$—), or butylene (that is, —$C_4H_8$—); x is 0–40; y is 0–40; the sum (x+y) is 0–40; and $R^T$ is straight, branched or cyclic alkyl containing 4 to 12 carbon atoms. Preferably, $R^T$ contains 7–12 or even 7–9 carbon atoms.

The alkylene residue $R^T$ in structural formula (T) represents a saturated, straight-chain, branched-chain, or cyclic moiety containing 4 to 12 carbon atoms. It is preferred that $R^T$ is branched, wherein the term "branched" is intended to encompass structures having one side alkyl chain, more than one side alkyl chain, or one or more side alkyl chains, one or more of which is itself branched. Branched structures include cyclic structures substituted with one or more alkyl groups, the alkyl groups being straight or branched. Examples of suitable $R^T$ groups include such groups as —$CH_2CH_2CH_2$—, —$C(CH_3)_2CH_2$—, —$CH_2CH(CH_2CH_2CH_3)$—, —$(CH_2)_6$—, —$CH_2C(CH_3)_2CH_2$—, —$CH_2CH(CH_3)CH_2$—, —$CH_2C(CH_3)_2CH(CH(CH_3)_2)$—, —$CH_2CH(CH_2CH_3)CH_2CH_2CH_2CH_2$—, and

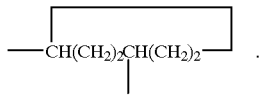

In the alkoxylated diols, the number of repeating units in each poly(alkoxy) chain can be up to 40 but it is preferred that each chain contains 1 to 10 repeating alkoxy units or more preferably 1 to 5 alkoxy units. The preferred alkoxy chains are poly(ethoxy), or are composed of 1 to 2 ethoxy units capped with a chain of 1 to 5 propoxy units.

Compounds of structural formula (T) defined above are in many instances commercially available. Compounds of structural formula (T) can be prepared in straightforward manner familiar to those of ordinary skill in this art by obtaining or preparing the corresponding precursor diol of structural formula HO—$R^T$—OH, and then alkoxylating the precursor diol with a stoichiometrically appropriate number of moles of the desired corresponding alkylene oxide, such as ethylene oxide, propylene oxide, and/or butylene oxide. In those cases where it is desired to alkoxylate only one of the hydroxyl groups on the precursor diol, in some embodiments the alkoxylation will preferentially occur at only one of the hydroxyl groups, particularly where one of them is a primary hydroxyl and the other is a secondary hydroxyl. However, in those cases where both hydroxyl groups on the precursor diol might tend to alkoxylate but alkoxylation at only one of the hydroxyl groups is desired, the hydroxyl group at which alkoxylation is desired not to occur can be protected by preliminarily reacting it with a suitable protecting group such as a lower alkyl moiety or an esterifying substituent. Thereafter, following the alkoxylation, the protecting group is removed in a known manner.

Preferred examples of compounds of the foregoing structural formula (T) include any one, or mixtures, of 2,2,4-trimethyl-1,3-pentanediol (TMPD) and/or 2-ethylhexane-1,3-diol, and/or the reaction product of TMPD and/or 2-ethylhexane-1,3-diol with 1 to 10 moles of ethylene oxide, and preferably with 1 to 5 moles of ethylene oxide, as well as analogs alkoxylated with other $C_3$ or $C_4$ alkyl oxides or mixtures of any of $C_2$, $C_3$ and/or $C_4$ alkyl oxides. Since the diol which is alkoxylated includes one primary hydroxyl group and one secondary hydroxyl group, the alkoxylation proceeds predominantly at the primary hydroxyl group.

The compositions which contain one or more compounds of structural formula (1) can also contain one or a mixture of compounds of structural formula (E)

$$R^{E1}—C(O)O—R^{E2}—(OC(O)R^{E3})_{0-1} \quad (E)$$

wherein $R^{E1}$ is straight, cyclic or branched alkyl containing 1–15 carbon atoms, and $R^{E1}$ is substituted with 0 to 3 hydroxyl groups; and wherein $R^{E2}$ is straight, cyclic or branched alkyl containing 1 to 10 carbon atoms, and $R^{E2}$ is substituted with 0 to 3 hydroxyl groups, and $R^{E2}$ can optionally be substituted with a group of the structure —OC(O)—$R^{E3}$ wherein $R^{E3}$ is straight, cyclic or branched alkyl containing 1 to 15 carbon atoms and is optionally substituted with a hydroxyl group.

Preferred compounds of structural formula (E) include those wherein $R^{E2}$ contains 2 or 3 carbon atoms, for example, glycol and glyceryl derivative, or $R^{E2}$ contains about 8 carbon atoms, for example, derivatives of 2,2,4trimethylpentanediol or of 2-ethylhexanediol. Preferred compounds of structural formula (E) include 2,2,4-trimethyl-1,3-pentanediol monoisobutyrate, hydroxypivalyl hydroxypivalate, and the monoester of TMPD with hydroxypivalic acid.

Formulations can also contain what may be termed aesthetic additives to provide properties such as fragrance, preservative, viscosity control, and color. Such additives are discussed below. The formulations according to the present invention generally exhibit highly satisfactory viscosities, generally as pourable and even sprayable fluids.

G. ADDITIONAL SURFACTANTS

Other suitable non-quaternary compound surfactants, whether anionic, cationic, zwitterionic, nonionic, or amphoteric, may be used in combination with the compounds and formulations of the invention, depending on the application.

1. General Surfactants

For example, in a fabric softening application, suitable anionic surfactants may include, without limitation, the alkylbenzene sulfonates, α-olefin sulfonates, and xylene sulfonates available from Witco Corporation under the WITCONATE® trademark. While these surfactants may be unsuitable for personal care applications because they may cause skin and eye irritation, surfactants suitable for personal care applications may be used in other non-personal care applications.

2. Personal Care Surfactants

For personal care applications, suitable anionic surfactants would include, without limitation, ammonium lauryl sulfate, sodium lauryl sulfate, any α-olefin sulfonate, ammonium laureth sulfate (2 or 3 moles), sodium laureth sulfate (2 or 3 moles), sodium myristyl sulfate, sodium myristeth sulfate (1–4 moles), ammonium xylene sulfonate, sodium xylene sulfonate, TEA dodecylbenzene sulfonate, TEA lauryl sulfate, ammonium pareth sulfate, sodium pareth sulfate, sodium oleth sulfate, derivatives of any of the forgoing, and similar compounds known to those of skill in the art, and mixtures thereof. For personal care applications, suitable amphoteric surfactants or non-ionic surfactants include betaines, sulfosuccinates, mono- and diglycerides, glycinates, sugars and derivatives thereof, hydroxysultaines, mono- and diacetates, ethoxylated derivatives of any of the forgoing, and similar compounds known to those of skill in the art, and mixtures thereof. Preferred surfactants include cocamidopropyl betaine, lauramidopropyl betaine, ricinoleamidopropyl betaine, myristamidopropyl betaine, palmamidopropyl betaine, stearamidopropyl betaine, behenamidopropyl betaine, erucamidopropyl betaine, cocamidopropyl hydroxysultaine, myristamidopropyl hydroxysultaine, palmamidopropyl hydroxysultaine, stearamidopropyl hydroxysultaine, behenamidopropyl hydroxysultaine, erucamidopropyl hydroxysultaine, disodium lauroamphodiacetate, disodium cocamphodiacetate, disodium myristamphodiacetate, disodium palmamphodiacetate, disodium stearamphodiacetate, disodium behenamphodiacetate, disodium erucamphodiacetate, sodium lauryl amphoacetate, sodium cocamphoacetate, sodium cocoamphopropionate, sodium laurylamphopropionate, disodium lauroamphodipropionate, sodium lauryl sulfosuccinate, disodium laureth sulfosuccinate, cocobetaine, laurylbetaine, myristylbetaine, stearylbetaine, behenylbetaine, PEG 1-300 glyceryl cocoate, PEG 1-300 glyceryl tallowate, PEG 1-500 hydrogenated glyceryl palmitate, coco-glucoside, lauryl glucoside, decyl glucoside, and mixtures thereof.

Other surfactants that may be added to these systems include, but are not limited to, alkanolamides such as almondamide diethanolamine (DEA), behenamide DEA, cocamide DEA, hydrogenated tallowamide DEA, isostearamide DEA, lactamide DEA, lauramide DEA, linoleamide DEA, myristamide DEA, oleamide DEA, palmamide DEA, palmitamide DEA, ricinoleamide DEA, soyamide DEA, stearamide DEA, tallamide DEA, and tallowamide DEA. Preferred alkanolamides include acetamide monoethanolamine (MEA), behenamide MEA, cocamide MEA, hydroxystearamide MEA, isostearamide MEA, lactamide MEA, lauramide MEA, linoleamide MEA, myristamide MEA, oleamide MEA, palrnamide MEA, palmitamide MEA, ricinoleamide MEA, stearamide MEA, tallowamide MEA, undecylenamide MEA, cocamide monoisopropylamine (MIPA), hydroxyethyl stearamide MIPA, isostearamide MIPA, lauramide MIPA, linoleamide MIPA, myristamide MIPA, oleamide MIPA, palinnide MIPA, ricinoleamide MIPA, and stearamide MIPA. Some of these alkanolamides are available from Witco Corporation under the WITCAMIDE® tradename.

In addition, various amine oxides may be used in these systems. Preferred amine oxides include, but are not limited to, behenamine oxide, cocamidopropylamine oxide, cocamine oxide, decylamine oxide, dihydroxyethylcocamine oxide, dihydroxyethyllauramine oxide, dihydroxyethyltallowamine oxide, hydrogenated palm kernel amine oxide, hydrogenated tallowamine oxide, isostearamidopropylamine oxide, lauramidopropylamine oxide, lauramine oxide, myristamidopropylamine oxide, myristamine oxide, oleamidopropylamine oxide, oleamine oxide, palmitamidopropylamine oxide, palmitamine oxide, soyamidopropylamine oxide, stearamidopropylamine oxide, stearamine oxide, tallowamidopropylamine oxide, tallowamine oxide, and undecylenamidopropylamine oxide. Several of these materials are available from Witco Corporation under the VAROX® tradename.

H. PERSONAL CARE EMOLLIENTS AND EMULSIFIERS

Emollients and emulsifiers are also typically used in personal care formulations in combination with the polyester amine compounds and polyquaternary compounds of the invention, depending on the application.

1. Personal Care Emollients

The preferred embodiment of this invention may also be used in emulsions that can be used as skin or hair conditioners which can take the form of lotions, creams, leave-on products, and rinse-off products. These systems may also include additional products that may improve the feel and conditioning, or the emolliency of skin and hair. In addition to some of the materials mentioned above that can also function as conditioning agents, preferred additives for this use include, but are not restricted to, acetylated lanolin, aminopropyl dimethicone, ammonium hydrolyzed collagen, ammonium lauroyl sarcosinate, amodimethicone, amodimethicone/dimethicone copolyol, amodimethicone hydroxystearate, capryloyl hydrolyzed collagen, cetyl alcohol, cetyl esters, cetyl laurate, cocamidopropyl dimethylamine dihydroxymethylpropionate, cocoyl hydrolyzed soy protein, collagen, disodium cocoamphodiacetate, disodium cocoamphodipropionate, dioctyl dimerate, ditridecyl adipate, glycerine, glyceryl oleate, glyceryl stearate, hydrogenated soybean oil, hydrogenated tallow glycerides, isocetyl stearate, jojoba (*Buxus chinensis*) oil, keratin, lanolin, milk protein, mineral oil, oat (*Avena saliva*) protein, octyl cocoate, oleyl myristate, oleyl stearate, palm alcohol, palm glycerides, panthenol, PEG-10, PEG-32, PEG-100, PEG-200, petrolatum, PPG-6-sorbeth-245, stearyl citrate, tridecyl stearate, urea. vegetable oil, and wheat amino acids. Some of these products are available from Witco Corporation under the KEMSTRENE®, WITCONOL™, STARFOL®, and KEMESTER® tradenames.

2. Personal Care Emulsifiers

Such emulsions usually include emulsifiers to form and preserve the emulsion. In addition to some of the materials previously mentioned that also act as emulsifiers, some preferred emulsifiers for this use include, but are not restricted to beheneth-5, beheneth-10, beheneth-20, butylglucoside caprate, ceteareth-2, ceteareth-10, ceteareth-18, ceteth-10, ceteth-16, corn oil PEG-8 esters, $C_{9-11}$ pareth-3, $C_{11-15}$ pareth-5, $C_{11-15}$ pareth-12, $C_{12-13}$ pareth-2, $C_{12-13}$ pareth-10, $C_{12-13}$ parth-15, deceth-4, deceth-5, deceth-6, di-$C_{12-13}$ pareth-6 phosphate, di-$C_{12-15}$ pareth-8 phosphate, glyceryl cocoate, glyceryl laurate, glyceryl oleate, isoceteth-10, isodeceth-6, isosteareth-10, laureth-4, laureth-5, laureth-10, octyldodeceth-10, octyldodeceth-20, oleoyl ethyl glucoside, oleth-2, oleth-4, PEG-8 caprate, PEG-8 castor oil, PEG-7 cocamide, PEG-11 cocamide, PEG-15 cocoate, PEG-20 dilaurate, PEG-32 dilaurate, PEG-8 dioleate, PEG-2 distearate, PEG-8 distearate, PEG-8 glyceryl laurate, PEG-15 glyceryl laurate, PEG-4 isostearate, PEG-4 laurate, PEG-5 octanoate, PEG-9 oleamide, PEG-5 oleate, PEG-20 palmitate, PEG-6 stearate, PEG-16 tallate, polysorbate 20, polysorbate 80, steareth-10, trideceth-5, and undeceth-9.

I. OTHER ADDITIVES

Other additives and adjuvants can be optionally added to the compounds and formulations of the present invention for their known purposes. Such additives and adjuvants include, but are not limited to, perfumes, preservatives including bacteriocides and fungicides, insect and moth repelling agents, polymeric soil release agents, antistatic agents, dyes and colorants, especially bluing agents, viscosity control agents, antioxidants, silicones, defoaming agents, antifoaming agents, emulsifiers, brighteners, opacifiers, freeze-thaw control agents, shrinkage control agents, aloe, humectants, skin protectants, feel modifiers, waxes, glycerine, vitamins and extracts, and mixtures thereof. The identity and amounts of the additives and adjuvants used would depend on the application of the formulation and its desired properties. The additives and adjuvants are well-known to those of skill in the art and the additives and adjuvants listed below are not meant to be an exhaustive list but merely a guide to the types of additives that would typically be used.

1. Perfumes

As noted above, perfumes or fragrance materials may be added to the compositions and formulations of the present invention. The selection of the perfume or perfumes is based upon the application, the desired effect on the consumer, and preferences of the formulator. The perfume selected for use in the compositions and formulations of the present invention contains ingredients with odor characteristics which are preferred in order to provide a fresh impression on the surface to which the composition is directed, for example, those which provide a fresh impression for fabrics if a fabric softener treatment formulation is prepared. Such perfume is preferably present at a level of from about 0.01% to about 5%, preferably from about 0.05% to about 3%, more preferably from about 0.1% to about 2%, by weight of the total composition.

Preferably, the perfume is composed of fragrance materials selected from the group consisting of aromatic and aliphatic esters having molecular weights from about 130 to about 250; aliphatic and aromatic alcohols having molecular weights from about 90 to about 240; aliphatic ketones having molecular weights from about 150 to about 260; aromatic ketones having molecular weights from about 150 to about 270; aromatic and aliphatic lactones having molecular weights from about 130 to about 290; aliphatic aldehydes having molecular weights from about 140 to about 200; aromatic aldehydes having molecular weights from about 90 to about 230; aliphatic and aromatic ethers having molecular weights from about 150 to about 270; and condensation products of aldehydes and amines having molecular weights from about 180 to about 320; and mixtures thereof. Examples of such perfumes or fragrance materials include, but are not limited to: adoxal (2,6,10-trimethyl-9-undecen-1-al), allyl amyl glycolate, allyl cyclohexane (allyl-3-cyclohexylpropionate), amyl acetate (3-methyl-1-butanol), amyl salicylate, anisic aldehyde (4-methoxybenzaldehyde), aurantiol (condensation product of methyl anthranilate and hydroxycitronellal), bacdanol (2-ethyl-4-(2,2,3-trimethyl-3-cyclopenten-1-yl)-2-buten-1-ol), benzaldehyde, benzophenone, benzyl acetate, benzyl salicylate, β-damascone (1-(2,6,6-trimethyl-1-cyclohexen-1-yl)-2-buten-1-one, β,γ-hexanol (3-hexen-1-ol), buccoxime (1,5-dimethyl-oximebicyclo[3,2,1]octan-8-one), cedrol (octahydro-3,6,8,8-tetramethyl-1H-3A,-7-methanoazulen-6-ol), cetalox (dodecahydro-3A,6,-6,9A-tetramethylnaphtho[2,1B]furan), cis-3-hexenyl acetate, cis-3-hexenyl salicylate (β,γ-hexenyl salicylate), citronellol (3,7-dimethyl-6-octenol), citronellyl nitrile (geranyl nitrile), clove stem oil, coumarin, cyclohexyl salicylate, cymal (2-methyl-3-(p-isopropylphenyl)-propionaldehyde), decyl aldehyde, δ-damascone (1-(2,6,6-trimethyl-3-cyclohexen-1-yl)-2-buten-1-one), dihydromyrcenol (2,6-dimethyl-7-octan-2-ol), dimethyl benzyl carbinyl acetate, ethyl vanillin, ethyl-2-methyl butyrate, ethylene brassylate (ethylene tridecan-1,13-dioate), eucalyptol (1,8-epoxy-p-menthane), eugenol (4-allyl-2-methoxyphenol), exaltolide (cyclopentadecanolide), flor acetate (dihydronorcyclopentadienyl acetate), florhydral (3-(3-isopropylphenyl)butanal), frutene (dihydronorcyclopentadienyl propionate), galaxolide (1,3,4,6,7,8-hexahydro-4,6,6,7,8,8-hexamethylcyclopent-γ-2-benzopyrane), γ-decalactone (4-N-heptyl-4-hydroaldehyde), cinnamic aldehyde, hexyl salicylate, hydroxyambran (2-cyclododecylpropanol), hydroxycitronellal, α-ionone (4-(2,6,6-trimethyl-1-cyclohexenyl-1-yl)-3-buten-2-one), β-ionone (4-(2,6,6-trimethyl-1-cyclohexene-1-yl)-3-butene-2-one), γ-ionone (4-(2,6,6-trimethyl-2-methylcyclohexyl-1-yl)-3-methyl-3-buten-2-one), iso E super (7-acetyl-1,2,3,4,5,6,7,8-octahydro-1,1,6,7-tetramethylnaphthalene), isoeugenol (2-methoxy-4-(1-propenyl)-phenol), isojasmone (2-methyl-3-(2-pentenyl)-2-cyclopenten-1-one), koavone (acetyl diisoamylene), lauric aldehyde, lavandin, lavender, natural lemon CP (major component d-limonene), d-limonene/orange terpenes (1-methyl-4-isopropenyl-1-cyclohexene), linalool (3-hydroxy-3,7-dimethyl-1,6-octadiene), linalyl acetate (3-hydroxy-3,7-dimethyl-1,6-octadiene acetate), Irg 201 (2,4-dihydroxy-3,6-dimethyl benzoic acid methyl ester), lyral (4-(4-hydroxy-4methyl-pentyl)-3-cyclohexene-1-carboxaldehyde), majantol (2,2-dimethyl-3-(3-methylphenyl)-propanol), mayol (4-(1-methylethyl)-cyclohexanemethanol), methyl anthranilate (methyl-2-aminobenzoate), methyl-β-naphthyl ketone, methyl cedrylone (methyl cedrenyl ketone), methyl chavicol (1-methyloxy-4,2-propen-1-yl benzene), methyl dihydrojasmonate, methyl nonyl acetaldehyde, musk indanone (4-acetyl-6-tert-butyl-1,1-dimethylindane), nerol (2-cis-3,7-dimethyl-2,6-octadien-1-ol), nonalactone (4-hydroxynonanoic acid lactone), norlimbanol (1-(2,2,6-trimethyl-cyclohexyl)-3-hexanol), orange CP (major component d-limonene), P. T. bucinal (2-methyl-3(p-tert-butylphenyl)-propionaldehyde), p-hydroxyphenylbutanone, patchouli, phenyl acetaldehyde (1-oxo-2-phenylethane), phenyl acetaldehyde, dimethyl acetal, phenyl ethyl acetate, p-menth-1-en-8-ol, p-menth-1-en-1-ol, terpinyl acetate p-menth-1-en-8-yl acetate), tetrahydrolinalool (3,7-dimethyl-3-octanol), tetrahydromyrcenol (2,6-dimethyl-2-octanol), tonalid/musk plus (7-acetyl-1,1,3,4,4,6-hexamethyltetralin), undecalactone (4-N-heptyl-4-hydroxybutanoic acid lactone), undecavertol (4-methyl-3-decen-5-ol), undecanal, undecylenic aldehyde, vanillin (4-hydroxy-3-methoxybenzaldehyde), verdox (2-ter-butyl cyclohexyl acetate), vertenex (4-tert-butyl cyclohexyl acetate), and mixtures thereof.

The selection of such perfumes and fragrance materials are well-known to those of skill in the art, both for desired scent and appropriate scent impact. For example, when high initial perfume odor impact on fabrics is desired, it is preferable to select a perfuune containing perfume ingredients which are not too hydrophobic. The degree of hydrophobicity of a perfume ingredient can be correlated with its octanol/water partitioning coefficient P, the ratio between its equilibrium concentration in octanol and in water. Thus, a perfume ingredient with a greater partitioning coefficient P is more hydrophobic and a perfume ingredient with a smaller partitioning coefficient P is more hydrophilic; a selection based on the application and intended effect may be made accordingly. For example, in a fabric application, the preferred perfume ingredients would have an octanol/water partitioning coefficient P of about 1,000 or smaller.

2. Preservatives

Optionally, solubilized, water-soluble preservatives can be added to the present invention. Preservatives are especially preferred when organic compounds that are subject to microorganisms are added to the compositions of the present invention, especially when they are used in aqueous compositions. When such compounds are present, long term and even short term storage stability of the compositions and formulations becomes an important issue since contamination by certain microorganisms with subsequent microbial growth often results in an unsightly and/or malodorous solution. Therefore, because microbial growth in these compositions and formulations is highly objectionable when it occurs, it is preferable to include a solubilized water-soluble, antimicrobial preservative, which is effective for inhibiting and/or regulating microbial growth in order to increase storage stability of the preferably clear and often aqueous compositions and formulations of the present invention.

Typical microorganisms that can be found personal care products include bacteria, for example, *Bacillus thuringiensis* (cereus group) and *Bacillus sphaericus*, and fungi, for example, *Aspergillus ustus*. *Bacillus sphaericus* is one of the most numerous members of Bacillus species in soils. In addition, microorganisms such as *Escherichia coli* and *Pseudomonas aerupinosa* are found in some water sources, and can be introduced during the preparation of aqueous solutions of the present invention.

It is preferable to use a broad spectrum preservative, for example, one that is effective on both bacteria (both gram positive and gram negative) and fungi. A limited spectrum preservative, for example, one that is only effective on a single group of microorganisms, for example, fungi, can be used in combination with a broad spectrum preservative or other limited spectrum preservatives with complimentary and/or supplementary activity. A mixture of broad spectrum preservatives can also be used.

Antimicrobial preservatives useful in the present invention can be biocidal compounds, that is, substances that kill microorganisms, or biostatic compounds, that is, substances that inhibit and/or regulate the growth of microorganisms. Preferred antimicrobial preservatives are those that are water-soluble and are effective at low levels. In general, the water-soluble preservatives that may be used include organic sulfur compounds, halogenated compounds, cyclic organic nitrogen compounds, low molecular weight aldehydes, quaternary compounds, dehydroacetic acid, phenyl and phenoxy compounds, and mixtures thereof. Examples of preservatives useful in the present invention include, but are not limited to, the short chain alkyl esters of p-hydroxybenzoic acid (commonly known as parabens); N-(4-chlorophenyl)-N-(3,4-dichlorophenyl) urea (also known as 3,4,4'-trichlorocarbanilide or triclocarban); 2,4,4'-trichloro-2'-hydroxydiphenyl ether, commonly known as triclosan); a mixture of about 77% 5-chloro-2-methyl-4-isothiazolin-3-one and about 23% 2-methyl-4-isothiazolin-3-one, a broad spectrum preservative available from the Rohm and Haas Company as a 1.5% aqueous solution under the tradename KATHON® CG; 5-bromo-5-nitro-1,3-dioxane, available from Henkel Corporation under the tradename BRONIDOX® L; 2-bromo-2-nitropropane-1,3-diol, available from Inolex Chemical Company under the tradename BRONOPOL™; 1,1'-hexamethylenebis(5-p-(chlorophenyl)biguanide) (commonly known as chlorhexidine) and its salts, for example, with acetic and digluconic acids; a 95:5 mixture of 1,3-bis(hydroxymethyl)-5,5-dimethyl-2,4-imidazolidinedione and 3-butyl-2-iodopropynyl carbamate, available from Lonza Inc. under the tradename GLYDANT® Plus; N-[1,3-bis (hydroxymethyl)2,5-dioxo-4-imidazolidinyl]-N,N'-bis (hydroxy-methyl) urea, commonly known as diazolidinyl urea, available from Sutton Laboratories, Inc. under the tradename GERMALL® II; N,N"-methylenebis[N'-[1-(hydroxymethyl)-2,5-dioxo-4-imidazolidinyl]urea] (commonly known as imidazolidinyl urea), available, for example, from 3V-Sigma under the tradename ABIOL™, from Induchem under the tradename UNICIDE® U-13, and from Sutton Laboratories, Inc. under the tradename GERMALL® 115; polymethoxy bicyclic oxazolidine, available from Huls America Inc. under the tradename NUOSEPT®; formaldehyde; glutaraldehyde; polyaminopropyl biguanide, available from ICI Americas, Inc. under the tradename COSMOCIL® CQ or from Brooks Industries Inc. under the tradename MIKROKILL™; dehydroacetic acid; and mixtures thereof. In general, however, the preservative can be any organic preservative material which is appropriate for the application, for example, in a fabric softening application such preservative will preferably not cause damage to fabric appearance, for example, discoloration, coloration, or bleaching of the fabric.

If the antimicrobial preservative is included in the compositions and formulations of the present invention, it is preferably present in an effective amount, wherein an "effective amount" means a level sufficient to prevent spoilage or prevent growth of inadvertently added microorganisms for a specific period of time. Preferred levels of preservative are from about 0.0001% to about 0.5%, more preferably from about 0.0002% to about 0.2%, most preferably from about 0.0003% to about 0.1%, by weight of the composition.

Bacteriostatic effects can sometimes be obtained for aqueous compositions by adjusting the composition pH to an acid pH, for example, less than about pH 4, preferably less than about pH 3. Low pH for microbial control is not a preferred approach in the present invention because the low pH can cause chemical degradation of the cyclodextrins. Therefore, aqueous compositions of the present invention should have a pH greater than about 3.0, preferably greater than about 4.0, more preferably greater than about 4.5. As stated above, it is preferable to use the preservative at an effective amount, as defined hereinabove. Optionally, however, the preservative can be used at a level which provides an antimicrobial effect on the treated fabrics.

3. Antistatic Agents

The composition of the present invention can optionally contain an effective amount of antistatic agent to provide the treated clothes with in-wear static. Preferred antistatic agents are those that are water soluble in at least effective amount, such that the composition remains a clear solution. Examples of these antistatic agents include monoalkyl cationic quaternary ammonium compounds, for example, mono ($C_{10}$–$C_{14}$ alkyl)trimethyl ammonium halide, such as monolauryl trimethyl ammonium chloride, hydroxycetyl hydroxyethyl dimethyl ammonium chloride (available from Henkel Corporation under the tradename DEHYQUART® E), and ethyl bis(polyethoxyethanol) alkylammonium ethylsulfate (available from Witco Corporation under the tradename VARIQUAT® 66), polyethylene glycols, polymeric quaternary ammonium salts (such as those available from Rhône-Poulenc Corporation under the MIRAPOL® tradename), quaternized polyethyleneimines, vinylpyrrolidone/methacrylamidopropyltrimethylammonium chloride copolymer (available from GAF Corporation under the tradename GAFQUAT® HS-100), triethonium hydrolyzed collagen ethosulfate (available from Maybrook Inc. under the tradename QUAT-PRO™ E), and mixtures thereof.

It is preferred that a no foaming, or low foaming, agent is used, to avoid foam formation during fabric treatment. It is also preferred that polyethoxylated agents such as polyethylene glycol or VARIQUAT® 66 are not used when α-cyclodextrin is used. When an antistatic agent is used it is typically present at a level of from about 0.05% to about 10%, preferably from about 0.1% to about 5%, more preferably from about 0.3% to about 3%, by weight of the composition.

4. Dyes and Colorants

Colorants and dyes, especially bluing agents, can be optionally added to the compositions of the present invention for visual appeal and performance impression. When colorants are used, they are used at extremely low levels to avoid fabric staining. Preferred colorants for use in the present compositions are highly water-soluble dyes, for example, LIQUITINT® dyes available from Milliken Chemical Company. Non-limiting examples of suitable dyes are, LIQUITINT® Blue HP, LIQUITINT® Blue 65, LIQUITINT® Patent Blue, LIQUITINT® Royal Blue, LIQUITINT® Experimental Yellow 8949-43, LIQUITINT® Green HMC, LIQUITINT® Yellow II, and mixtures thereof. Any dye can be used in the compositions of the present invention, but nonionic dyes are preferred to decrease interaction with dye transfer inhibitor. Useful acid dyes include: Polar Brilliant Blue, and D&C Yellow #10, both supplied by Hilton Davis Chemical Company. Nonionic LIQUITINT® dyes supplied by Milliken Chemical Company are also useful.

For many personal care products using the present invention, colorants are also added at extremely low levels.

Color additives for products to be marketed in the United States are named in compliance with Title 21 of the U.S. Code of Federal Regulations. Suitable colors include, but are not limited to, Acid Black 1, Acid Blue 3, Acid Blue 9 Aluminum Lake, Acid Blue 74, Acid Green 1, Acid Orange 6, Acid Red 14 Aluminum Lake, Acid Red 27, Acid Red 27 Aluminum Lake, Acid Red 51, Acid Violet 9, Acid Yellow 3, Acid Yellow 3 Aluminum Lake, Acid Yellow 73, Aluminum Powder, Basic Blue 6, Basic Yellow 11, β-Carotene, Brilliant Black 1, Bromocresol Green, Chromium Oxide Greens, CI 12010, CI 12120, CI 28440, CI 71105, Curry Red, D&C Blue No. 1 Aluminum Lake, D&C Blue No. 4, D&C Brown No. 1, D&C Green No. 3 Aluminum Lake, D&C Green No. 5, D&C Orange No. 4 Aluminum Lake, D&C Red No. 6, D&C Red No. 6 Aluminum Lake, D&C Violet No. 2, D&C Yellow No. 7, D&C Yellow No. 11, D&C Blue No. 1, FD&C Yellow No. 5 Aluminum Lake, iron oxides, Pigment Orange 5, Pigment Red 83, Pigment Yellow 73, Solvent Orange 1, Solvent Yellow 18, ultramarines, and zinc stearate.

5. Insect and Moth Repelling Agents

The composition of the present invention can optionally contain an effective amount of insect or moth repelling agents. Typical insect and moth repelling agents are pheromones, such as anti-aggregation pheromones, and other natural and/or synthetic ingredients. Preferred insect and moth repellent agents useful in the composition of the present invention are perfume ingredients, such as citronellol, citranellal, citral, linalool, cedar extract, geranium oil, sandalwood oil, 2-(diethylphenoxytethanol, 1-dodecene, and the like. Other examples of insect and/or moth repellents useful in the composition of the present invention are disclosed in U.S. Pat. Nos. 4,449,987; 4,693,890; 4,696,676; 4,933,371; 5,030,660; and 5,196,200; and in B. D. Mookherjee et al., "Semio Activity of Flavor and Fragrance Molecules on Various Insect Species", published in *Bioactive Volatile Compounds from Plants*, ASC Symposium Series 525, R. Teranishi, R. G. Buttery, and H. Sugisawa (eds.), 1993, pp. 35–48. All of these patents and publications are herein incorporated by reference in their entireties. When an insect and/or moth repellent is used it is typically present at a level of from about 0.005 wt. % to about 3 wt. % of the composition.

6. Polymeric Soil Release Agents

Soil release agents, usually polymers, are especially desirable additives at levels of from about 0.05 wt. % to about 5 wt. %, preferably from about 0.1 wt. % to about 4 wt. %, more preferably from about 0.2 wt. % to about 3 wt. %. Suitable soil release agents are disclosed in U.S. Pat. Nos. 4,702,857; 4,711,730; 4,713,194; 4,877,896; 4,956,447; and 4,749,596, all of these patents being herein incorporated by reference in their entireties.

Especially desirable optional ingredients are polymeric soil release agents comprising block copolymers of polyalkylene terephthalate and polyoxyethylene terephthalate, and block copolymers of polyalkylene terephthalate and polyethylene glycol. The polyalkylene terephthalate blocks preferably comprise ethylene and/or propylene groups. Many such soil release polymers are nonionic, for example, the nonionic soil release polymer is described in U.S. Pat. No. 4,849,257, which patent is herein incorporated by reference in its entirety.

The polymeric soil release agents useful in the present invention can include anionic and cationic polymeric soil release agents. Suitable anionic polymeric or oligomeric soil release agents are disclosed in U.S. Pat. No. 4,018,569, which patent is herein incorporated by reference in its entirety. Other suitable polymers are disclosed in U.S. Pat. No. 4,808,086, which patent is herein incorporated by reference in its entirety. Suitable cationic soil release polymers are described in U.S. Pat. No. 4,956,447, which patent has already been herein incorporated by reference.

7. Viscosity Control Agents

Viscosity control agents can be organic or inorganic in nature and may either lower or raise the viscosity of the formulation. Examples of organic viscosity modifiers (lowering) are aryl carboxylates and sulfonates (for example, benzoate, 2-hydroxybenzoate, 2-aminobenzoate, benzenesulfonate, 2-hydroxybenzenesulfonate, 2-aminobenzenesulfonate, etc.), fatty acids and esters, fatty alcohols, and water-miscible solvents such as short chain alcohols. Examples of inorganic viscosity control agents are water-soluble ionizable salts. A wide variety of ionizable salts can be used. Examples of suitable salts are the halides and acetates of ammonium ion and the group IA and IIA metals of the Periodic Table of the Elements, for example, calcium chloride, lithium chloride. sodium chloride, potassium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium acetate, potassium acetate, or mixtures thereof. Calcium chloride is preferred. The ionizable salts are particularly useful during the process of mixing the ingredients to make the compositions herein, and later to obtain the desired viscosity. The amount of ionizable salts used depends on the amount of active ingredients used in the compositions and can be adjusted according to the desire of the formulator. Typical levels of salts used to control the composition viscosity are from 0 to about 10 wt. %, preferably from about 0.01 wt. % to about 6 wt. %, and most preferably from about 0.02 wt. % to about 3 wt. % of the composition.

Viscosity modifiers (raising) or thickening agents can be added to increase the ability of the compositions to stably suspend water-insoluble articles, for example, perfume microcapsules. Such materials include hydroxypropyl substituted guar gum (such as that available from Rhône-Poulenc Corporation under the tradename JAGUAR® HP200), polyethylene glycol (such as that available from Union Carbide Corporation under the tradename CARBOWAX® 20M), hydrophobic modified hydroxyethylcellulose (such as that available from the Aqualon Company under the tradename NATROSOL® Plus), and/or organophilic clays (for example, hectorite and/or bentonite clays such as those available from the Rheox Company under the tradename BENTONE™ 27, 34 and 38 or from Southern Clay Products under the tradename BENTOLITE™ L; and those described in U.S. Pat. No. 4,103,047, which is herein incorporated by reference in its entirety). These viscosity raisers (thickeners) are typically used at levels from about 0.5 wt. % to about 30 wt. %, preferably from about 1 wt. % to about 5 wt. %, more preferably from about 1.5 wt. % to about 3.5 wt. %, and most preferably from about 2 wt. % to about 3 wt. %, of the composition.

8. Pearlizing and Opacifying Agents

Examples of pearlizing or opacifing agents that can be added to the compositions of this invention include, but are not restricted to, glycol distearate, propylene glycol distearate, and glycol stearate. Some of these products are available from Witco Corporation under the KEMESTER® tradename.

9. Vitamins and Extracts

In personal care applications, vitamins and extracts are often used in the formulations thereof. Examples of vitamins that can be added to the compositions of this invention include, but are not restricted to, vitamins $A_1$, $A_2$, $B_1$, $B_2$, $B_6$, $B_{12}$, C, D, E, H, and K, the provitamins, salts, derivatives, and complexes thereof, and mixtures thereof. Examples of extracts that can be added to the compositions of this invention include, but are not restricted to, rosemary extract, carrot extract, *Camelina sativa*, camomile extract, egg yolk extract, elm extract, acacia extract, rose extract, lilac extract, licorice extract, lemon extract, orange extract, lime extract, linden extract, melon extract, peach extract, orchid extract, orris extract, and the like, and mixtures thereof.

10. Antioxidants

Examples of antioxidants that can be added to the compositions of this invention are propyl gallate, available from Eastman Chemical Products, Inc. under the tradenames TENOX® PG and TENOX® S-1, and dibutylated hydroxytoluene, available from UOP Inc. under the tradename SUSTANE® BHT.

11. Silicones

The present compositions can contain silicones to provide additional benefits, for example, in a fabric application they may provide ease of ironing and improved fabric absorbency. As used herein, the term "silicones" comprises cationic and amphoteric silicones, polysiloxanes, and polysiloxanes having hydrogen-bonding functional groups consisting of amino, carboxyl, hydroxyl, ether, polyether, aldehyde, ketone, amide, ester, and thiol groups. Such polysiloxanes include, but are not limited to, polyether-modified polysiloxanes, amino-modified polysiloxanes, epoxy-modified polysiloxanes, polyhydrido-modified polysiloxanes, phenol-derivative-modified polysiloxanes, ABA-type polysiloxanes, $[AB]_N$-type polysiloxanes, amino $[AB]_N$-type polysiloxanes, including those available from OSi Specialties, Inc. (a division of Witco Corporation), under the SILWET®, NUWET®, NUDRY™, NUSOFT™, MAGNASOFT® tradenames.

Suitable silicones may include polydimethylsiloxanes of viscosity of from about 100 centistokes (cs) to about 100,000 cs, preferably from about 200 cs to about 60,000 cs and/or silicone gums. These silicones can be used in emulsified form, which can be conveniently obtained directly from the suppliers. Examples of these preemulsified silicones are the 60% emulsion of polydimethylsiloxane (350 cs) sold by Dow Corning Corporation under the tradename DOW CORNING® 1157 Fluid and the 50% emulsion of polydimethylsiloxane (10,000 cs) sold by General Electric Company under the tradename GENERAL ELECTRIC® SM 2140 silicones. The optional silicone component can be used in an amount of from about 0.1 wt. % to about 6 wt. % of the composition.

Silicone foam suppressants can also be used. These are usually not emulsified and typically have viscosities of from about 100 cs to about 10,000 cs, preferably from about 200 cs to about 5,000 cs. Very low levels are used, typically from about 0.01% to about 1%, preferably from about 0.02% to about 0.5%. Another preferred foam suppressant is a silicone/silicate mixture, for example, Dow Corning's ANTIFOAM™ A.

The pH (10% solution) of the compositions of this invention is generally adjusted to be in the range of from about 2 to about 7, preferably from about 2.4 to about 6.5, more preferably from about 2.6 to about 4. Adjustment of pH is normally carried out by including a small quantity of free acid in the formulation. Because no strong pH buffers are present, only small amounts of acid are required. Any acidic material can be used; its selection can be made by anyone skilled in the softener arts on the basis of cost, availability, safety, etc. Among the acids that can be used are methyl sulfonic, hydrochloric, sulfuric, phosphoric, citric, maleic, and succinic. For the purposes of this invention, pH is measured by a glass electrode in a 10% solution in water of the softening composition in comparison with a standard calomel reference electrode.

12. Lubrication and Slip Additives

Compositions and formulations of the present invention can contain additives such as water, insoluble organics such as fatty acids, fatty esters, triglycerides, oils, alcohols, fatty alcohols, fatty amines and derivatives, amides, hydrocarbons, mineral oils, waxes, and the like, and mixtures thereof, as lubrication and slip agents.

13. Dye Transfer Inhibitors

Compositions and formulations of the present invention can contain ethoxylated amines, amphoterics, betaines, polymers such as polyvinylpyrrolidone, and other ingredients that inhibit dye transfer.

14. Papermaking and Tissuemaking Additives

Paper and tissue softening or debonding compositions of the present invention would typically contain other chemicals commonly used in papermaking or tissuemaking, or to the paper or tissue furnish so long as they do not significantly and adversely affect the softening, absorbency of the fibrous material, and softness enhancing actions of the amine and quaternary ammonium softening compounds of the present invention.

A. Wetting Agents

The present invention may contain as an optional ingredient from about 0.005% to about 3.0%, more preferably from about 0.03% to 1.0% by weight, on a dry fiber basis of a wetting agent. Such wetting agents may be selected from polyhydroxy compounds, nonionic surfactants such as alkoxylated compounds and linear alkoxylated alcohols Examples of water soluble polyhydroxy compounds that can be used as wetting agents in the present invention include glycerol, polyglycerols having a weight-average molecular weight of from about 150 to about 800, and polyoxyethylene glycols and polyoxypropylene glycols having a weight-average molecular weight of from about 200 to about 4000, preferably from about 200 to about 1000, most preferably from about 200 to about 600. Polyoxyethylene glycols having an weight-average molecular weight of from about 200 to about 600 are especially preferred. Mixtures of the above-described polyhydroxy compounds may also be used. A particularly preferred polyhydroxy compound is polyoxyethylene glycol having an weight average molecular weight of about 400, available from Union Carbide Corporation under the tradename PEG-400.

Suitable nonionic surfactants can be used as wetting agents in the present invention. These include addition products of alkoxylating agents such as ethylene oxide (EO), propylene oxide (PO), isopropylene oxide (iPO), or butylene oxide (BO), or a mixture thereof, with fatty alcohols, fatty acids, fatty amines, etc. Any of the alkoxylated materials of the particular type described hereinafter can be used as the nonionic surfactant. Suitable compounds are substantially water-soluble surfactants of the general formula:

$$R_{10}-Y-(C_2H_4O)_z-C_2H_4OH$$

wherein $R_{10}$ for both solid and liquid compositions is selected from the group consisting of primary, secondary and branched chain alkyl and/or acyl hydrocarbyl groups; primary, secondary and branched chain alkenyl hydrocarbyl groups; and primary, secondary and branched chain alkyl- and alkenyl-substituted phenolic hydrocarbyl groups; the hydrocarbyl groups having a hydrocarbyl chain length of from about 8 to about 20, preferably from about 10 to about 18 carbon atoms. More preferably the hydrocarbyl chain length for liquid compositions is from about 16 to about 18 carbon atoms and for solid compositions from about 10 to about 14 carbon atoms. In the general formula for the ethoxylated nonionic surfactants herein, Y is typically —O—, —C(O)O—, —C(O)N($R_{11}$)—, or —C(O)N($R_{11}$)$R_{11}$—, in which $R_{10}$ and $R_{11}$, when present, have the meanings given hereinbefore, and/or $R_{11}$ can be hydrogen, and z is at least about 8, preferably at least about 10–11. Performance and, usually, stability of the softener composition decrease when fewer ethoxylate groups are present.

Examples of nonionic surfactants according to the above formula follow, wherein the integer in parenthesis identifies the number of EO groups in the molecule. In particular, the deco-, under-, dodder-, terraced-, and pentadecaethoxylates of n-hexadecanol and n-octadecanol are useful wetting agents in the context of this invention. Exemplary ethoxylated primary alcohols useful herein as the viscosity/dispersibility modifiers of the compositions are n-octadecanol EO(10); and n-decanol EO(11). The ethoxylates of mixed natural or synthetic alcohols in the "oleyl" chain length range are also useful herein. Specific examples of such materials include oleyl alcohol EO(11), oleyl alcohol EO(18), and oleyl alcohol EO(25). In addition, the deca-, undeca-, dodeca-, tetradeca-, pentadeca-, octadeca-, and nonadecaethoxylates of 3-hexadecanol, 2-octadecanol, 4-eicosanol, and 5-eicosanol can be used as wetting agents in the present invention.

As in the case of the alcohol alkoxylates, the hexa-through octadecaethoxylates of alkylated phenols, particularly monohydric alkylphenols, are useful as the viscosity/dispersibility modifiers of the instant compositions. In particular, the hex-through octadeca-ethoxylates of p-tridecylphenol, m-pentadecylphenol, and the like, are useful herein. Exemplary ethoxylated alkylphenols useful as the wetting agents of the mixtures herein are: p-tridecylphenol EO(11) and p-pentadecylphenol EO(18). As used herein and as generally recognized in the art, a phenylene group in the nonionic formula is the equivalent of an alkylene group containing from 2 to 4 carbon atoms. It should also be noted that the alkenyl alcohols, both priinary and secondary, and alkenyl phenols corresponding to those disclosed immediately hereinabove can be ethoxylated and used as wetting agents in the present invention. Furthermore, branched-chain primary and secondary alcohols, usually synthesized using the well-known Oxo Process, can be ethoxylated and can be used as wetting agents in the present invention.

The above ethoxylated nonionic surfactants are useful in the present compositions alone or in combination, and the term "nonionic surfactant" encompasses mixed nonionic surface active agents. The level of surfactant, if used, is preferably from about 0.01% to about 2.0% by weight, based on the dry fiber weight of the tissue paper. The surfactants preferably have alkyl chains with eight or more carbon atoms. Exemplary anionic surfactants are linear alkyl sulfonates, and alkylbenzene sulfonates. Exemplary nonionic surfactants are alkylglycosides including alkylglycoside esters such as that available from Croda, Inc. under the tradename CRODESTA™ SL-40; alkylglycoside ethers as described in U.S. Pat. No. 4,011,389, which patent is herein incorporated by reference in its entirety; and alkylpolyethoxylated esters such as those available from Lonza Inc. under the tradename PEGOSPERSE® 200 ML and available from Rhône-Poulenc Corporation under the tradename IGEPAL® RC-520.

B. Strength Additives

Other types of chemicals which may be added, include the strength additives to increase the dry tensile strength and the wet burst of the tissue webs. The present invention may contain as an optional component from about 0.01 wt. % to about 3.0 wt. %, more preferably from about 0.3 wt. % to about 1.5 wt. %, on a dry fiber weight basis, of a water-soluble strength additive resin. Such water-soluble strength additive resins may include dry strength additives, permanent wet strength resins, temporary wet strength resins, or a compatible mixture thereof.

Examples of suitable dry strength additives include carboxymethyl cellulose and cationic polymers from the ACCO chemical family such as ACCO 711 and ACCO 514, with ACCO chemical family being preferred. These materials are available commercially from the American Cyanamid Company.

As used herein, the term "permanent wet strength resin" refers to a resin which allows the paper sheet, when placed in an aqueous medium, to keep a majority of its initial wet strength for a period of time greater than at least two minutes. Permanent wet strength resins useful herein can be of several types. Generally, those resins which have previously found and which will hereafter find utility in the papermaking art are useful herein. Numerous examples are described by Westfelt in *Cellulose Chemistry and Technology*, Volume 13, at pages 813–825 (1979), which is herein incorporated by reference in its entirety. Usually, the wet strength resins are water-soluble, cationic materials. That is to say, the resins are water-soluble at the time they are added to the papermaking furnish. It is quite possible, and even to be expected, that subsequent events such as cross-linking will render the resins insoluble in water. Further, some resins are soluble only under specific conditions, such as over a limited pH range. Wet strength resins are generally believed to undergo a cross-linking or other curing reactions after they have been deposited on, within, or among the papermaking fibers. However, such cross-linking or curing does not normally occur so long as substantial amounts of water are present.

Of particular utility are the various polyamide-epichlorohydrin resins. These materials are low molecular weight polymers provided with reactive functional groups such as amino, epoxy, and azetidinium groups. The patent literature is replete with descriptions of processes for making such materials, for example, U.S. Pat. Nos. 3,700,623 and 3,772,076, both herein incorporated by reference in their entireties. Such polyamide-epichlorohydrin resins available from Hercules Inc. under the trademarks KYMENE® 557H and KYMENE® 2064 are particularly useful in this invention. In addition, base-activated polyamide-epichlorohydrin resins are generally described in U.S. Pat. Nos. 3,855,158; 3,899,388; 4,129,528; 4,147,586; and 4,222,921, which patents are herein incorporated by reference in their entireties. These materials are available from the Monsanto Company under the tradename SANTO-RES™, such as SANTO-RES™ 31.

Other water-soluble cationic resins useful herein are the polyacrylamide resins, such as those generally described in U.S. Pat. Nos. 3,556,932 and 3,556,933, which are both herein incorporated by reference in their entireties. Such materials are available from the American Cyanamid Company under the tradename PAREZ®, such as PAREZ® 631NC. Other types of water-soluble resins useful in the present invention include acrylic emulsions and anionic styrene-butadiene latexes, numerous examples of which are provided in U.S. Pat. No. 3,844,880, which is herein incorporated by reference in its entirety. Still other water-soluble cationic resins finding utility in this invention are the urea formaldehyde and melamine formaldehyde resins. These polyfunctional, reactive polymers have molecular weights on the order of a few thousand. The more common functional groups include nitrogen containing groups such as amino groups and methylol groups attached to nitrogen. Although less preferred, polyethylenimine-type resins find utility in the present invention. More complete descriptions of the aforementioned water-soluble resins, including their manufacture, can be found in TAPPI Monograph Series No. 29, *Wet Strength In Paper and Paperboard*, Technical Association of the Pulp and Paper Industry (New York: 1965), which is herein incorporated by reference in its entirety.

The above-mentioned permanent wet strength additives are those that produce paper products with permanent wet strength, that is, paper which when placed in an aqueous medium retains a substantial portion of its initial wet strength over time. However, permanent wet strength in some types of paper products can be an unnecessary and undesirable property. Paper products such as toilet tissues, etc., are generally disposed of after brief periods of use into septic systems and the like. Clogging of these systems can result if the paper product permanently retains its hydrolysis-resistant strength properties. Thus, manufacturers use temporary wet strength additives to paper products for which wet strength is sufficient for the intended use, but which then decays upon soaking in water. Decay of the wet strength facilitates flow of the paper product through septic systems.

Examples of suitable temporary wet strength resins include modified starch temporary wet strength agents, such as that available from the National Starch and Chemical Corporation under the tradename NATIONAL STARCH™ 78-0080. This type of wet strength agent can be made by reacting dimethoxyethyl-N-methyl-chloroacetamide with cationic starch polymers. Modified starch temporary wet strength agents are also described in U.S. Pat. Nos. 4,675,394 and 4,981,557, both of which are herein incorporated by reference in their entireties.

C. Other Additives

Other suitable additives may be used in paper and tissue-making applications, depending on the application. For example, glycerin may also be used in the composition and formulations thereof. If used, the amount of glycerin in the aqueous softening composition can be from about 0.1 wt. % to about 98 wt. %, more preferably from about 60 to about 80 wt. %, and still more preferably from about 40 to about 60 wt. %, of the composition. In addition, the compositions and formulations of the instant invention can contain glycols, such as propylene glycol or polyethylene glycol, instead of or in addition to glycerin in such formulations.

Other optional ingredients include aloe, humectants, skin protectants, and feel modifiers. Suitable humectants include lactic acid and its salts, sugars, ethoxylated glycerin, ethoxylated lanolin, corn syrup, hydrolyzed starch hydrolysate, urea, and sorbitol. Suitable skin protectants include allantoin, kaolin, and zinc oxide. Suitable feel modifiers include corn starch, oat flour, talc, boron nitride, and cyclodextrin.

J. EXAMPLES

The following examples are but a few examples of more particular formulations embodying the compositions of the present invention. The following examples are provided for purposes of further description of the present invention and are not intended to limit the scope of that which is regarded as the invention.

Basic Fabric Softener Formulations

Example 1

Hexamethylenediamine was reacted with 4 moles of ethylene oxide per mole of HMDA. The HMDA ethoxylate was esterified in two different runs with a mixture of $C_{14}$–$C_{18}$ fatty acids (2 moles of fatty acid per mole of ethoxylate) following which the HMDA ethoxylated ester was quaternized with 2 moles of DMS per mole of HMDA. In Run (1-A) the fatty acids were a commercial mixture of tallow fatty acids and in Run (1-B) the fatty acids were obtained from canola oil.

Example 2

This example illustrates formulations of compounds according to structural formula (1) in conventional solvent systems. A product was made by thoroughly blending the quaternary and solvent, then blending in the fragrance and then the water. The components and the amounts thereof were:

EXAMPLE 2

| Component | Amount (wt. %) |
|---|---|
| Product of Run 1-B (85 wt. % in isopropanol) | 23.5 |
| Solvent (hexylene glycol) | 18–20 |
| Fragrance, dye, preservative, and other additives | as needed |
| Deionized water | to 100 |

The resulting formulations had a cloud point of 45° C., a melting point above 10° C., and a Gardner color of above 0.5. The quaternary product of Run 1-B exhibits little or no gelation upon addition to water.

The above formulation was repeated except using a 50:50 (wt.) mixture of products prepared in accordance with Runs 1-A and 1-B. The resulting formulation has a cloud point of 50–55° C. and exhibits satisfactory properties.

Example 3

This example illustrates that clear formulations can be made which contain a conventional quaternary ammonium fabric softener compound together with one or a mixture of compounds of structural formula (1) as defined herein. This discovery is particularly unexpected in that many conventional quaternary ammonium fabric softener actives, such as the di($C_8$–$C_{22}$ alkyl/alkenyl) di($C_1$–$C_4$ alkyl) quaternary ammonium compounds, like the one employed in this example, cannot readily be formulated into a clear composition in an acceptable amount using existing solvent systems or solvent/coupling agent systems.

The composition of Example 3 was made using the procedure used in Example 2. The components and the amounts thereof were:

EXAMPLE 3

| Component | Amount (wt. %) |
|---|---|
| Product of Run 1-B, 85 wt. % in isopropanol | 14.1 |
| Ditallow dimethyl ammonium chloride (available from Witco Corporation as ADOGEN ® 470), 75 wt. % in isopropanol | 10.7 |
| Hexylene glycol | 24.0 |
| Fragrance, dye, preservative, and other additives | as needed |
| Deionized water | to 100 |

The resulting product has a cloud point of 45–50° C., and a melting point of 27° C. Its color is less than 0.5 Gardner.

Examples 4 and 5

Additional formulations employing another solvent system include Example 4 and Example 5, both made by the procedure disclosed in Example 2.

EXAMPLE 4

| Component | Amount (wt. %) |
|---|---|
| Product of Run 1-B | 23.5 |
| TMPD | 7.5 |
| Hexylene glycol | 7.5 |
| Fragrance, dye, preservative, and other additives | as needed |
| Deionized water | to 100 |

EXAMPLE 5

| Component | Amount (wt. %) |
|---|---|
| Product of Run 1-A | 11.8 |
| Product of Run 1-B | 11.8 |
| TMPD | 7.5 |
| Hexylene glycol | 7.5 |
| Fragrance, dye, preservative, and other additives | as needed |
| Deionized water | to 100 |

As noted above, fabric softening actives, such as amines and ammonium derivatives, are often rendered ineffective by reaction with the anionic detergent compounds present in the wash water. Although this is most obviously a problem if both detergent and softener compounds are added together in a wash cycle, even if the fabric softener is added during a rinse cycle (as is typically done), residual detergent compounds present in the fabric interferes with the softener.

Examples 6 and 7

More generally, exemplary formulation guidelines for fabric softener compositions which include polyester polyquaternary compounds conforming to structural formula (1), include Examples 6 and 7. As noted above, when a clear formulation is desired, the use of an unsaturated fatty acid is preferred to make the compound of structural formula (1) or at least a portion of the compound of structural formula (1) used in the formulation. If a clear formulation is desired, the I.V. of the fatty acid used to make the compound of structural formula (1) ranges from about 30 to about 140, more preferably the I.V. ranges from about 80 to about 120, most preferably the I.V. ranges from about 90 to about 110. Examples of some fatty acids that would be preferred may be derived from the following fats and oils: tallow, fish oils, canola (including fatty acids derived from partially hydrogenated canola), palm, wheat germ, rapeseed, olive, corn, neem, peanut, safflower, sesame seed, soybean, sunflower seed, and cocoa buffer.

EXAMPLE 6

Clear Polyester Polyquaternary in Conventional Solvent(s)

| Component | Amount (wt. %) |
|---|---|
| Compound of structural formula (1) | 15–20 |
| Solvent(s) (for example, isopropanol, hexylene glycol) | 20–30 |
| Fragrance, dye, preservative, and other additives | as needed |
| Deionized water | to 100 |

EXAMPLE 7

Clear Polyester Polyquaternary with Coupling Agent

| Component | Amount (wt. %) |
|---|---|
| Compound of structural formula (1) | 15–25 |
| Coupling agent(s) (for example, diol or alkoxylate of structural formula (T) and/or hydroxyester of structural formula (E)) | 10–15 |
| Acid (for example, HCl) | to pH 2.5–4 |
| Fragrance, dye, preservative, and other additives | as needed |
| Deionized water | to 100 |

Examples 8 to 13

As disclosed above, the compounds of structural formula (1) may be used either alone or in combination with other compounds. Such compounds may include conventional quats such as those set forth herein above (see E. ADDITONAL QUATERNARY AMMONIUM COMPOUNDS).

Indeed, some of these formulations provide advantageous formulations providing and synergistic or unexpected properties. For example, as explained above, detergent compounds are generally anionic surfactants and naturally tend to complex with or even precipitate out of solution when cationic softening ingredients are present in the same aqueous solution. This complexation or precipitation reaction interferes with the performance of both the detergent compounds and the softening compounds and is therefore undesirable. Detergents and softeners are therefore generally not added simultaneously in laundry operations to avoid this undesirable complexation or precipitation reaction; however, as North American washing machines typically rinse the clothes only once before fabric softener is added to the washload, even if the fabric softener is added during a rinse cycle (as is typically done), residual anionic detergent compounds present in the fabric complexes with the cationic softener compounds, often rendering about 15% to 30% or more of the softener inactive. It has been found that certain conventional quats, particularly the ester quats of structural formula (xxii), in combination with compounds of structural formula (1) provide an advantageous fabric softening formulation with surprising resistance to complexation with anionic surfactants.

EXAMPLE 8

High Solids HMDA Fabric Softener Formulation

| Component | Amount (wt. %) |
|---|---|
| HMDA + 4 moles EO + 2.5 moles tallow fatty acid + 2 moles DMS | 10 |
| Tallow-based TEA ester quat (DMS-based quat) | 15 |
| Fragrance, preservative, dye, and other additives | as needed, to 100 |

EXAMPLE 9

High Solids BHMT Fabric Softener Formulation

| Component | Amount (wt. %) |
|---|---|
| BHMT + 4 moles EO + 3 moles tallow fatty acid + 3 moles DMS | 10 |
| Tallow-based TEA ester quat (DMS-based quat) | 15 |
| Fragrance, preservative, dye, and other additives | as needed, to 100 |

EXAMPLE 10

High Solids BHMT Fabric Softener Formulation

| Component | Amount (wt. %) |
|---|---|
| BHMT + 5 moles EO + 2.5 moles tallow fatty acid + 3 moles DMS | 5 |
| Tallow-based MDEA ester quat (DMS-based quat) | 20 |
| Fragrance, preservative, dye, and other additives | as needed, to 100 |

EXAMPLE 11

High Solids BHMT Fabric Softener Formulation

| Component | Amount (wt. %) |
|---|---|
| BHMT + 5 moles EO + 3.5 moles tallow fatty acid + 3 moles DMS | 5 |
| Ditallow ester of 3-(dimethylamino)-1,2-propanediol (methyl chloride-based quat) | 10 |
| Fragrance, preservative, dye, and other additives | as needed, to 100 |

EXAMPLE 12

Low Solids HMDA Fabric Softener Formulation

| Component | Amount (wt. %) |
|---|---|
| HMDA + 4 moles EO + 2 moles tallow fatty acid + 2 moles DMS | 2.5 |
| Tallow-based TEA ester quat (DMS-based quat) | 5 |
| Fragrance, preservative, dye, and other additives | as needed, to 100 |

EXAMPLE 13

Low Solids BHMT Fabric Softener Formulation

| Component | Amount (wt. %) |
|---|---|
| BHMT + 5 moles EO + 2.5 moles tallow fatty acid + 2 moles DMS | 2 |
| Tallow-based MDEA ester chloride quat | 5 |
| Fragrance, preservative, dye, and other additives | as needed, to 100 |

There are many unexpected benefits of the above formulations. Most importantly, there is improved softening performance of the formulation over an equivalent amount of dialkyl ester quat formulation absent compounds of structural formula (1). In addition, however, the formulations above disperse readily into water, even cold water, without a viscosity increase as with conventional quats, and provide a finer final particle size when so dispersed, for example, at 100 ppm concentration. Moreover, the formulations have improved fluidity and viscosity, even in high solids formulations, over conventional non-blended formulations, exhibit reduced staining, and provide high color and odor stability. It should also be noted that certain of the formulations may be made clear, the provide clear compositions more readily (that is, over a greater concentration range with lower solvent concentrations) when the fatty acid levels of the polyester quat component is lower, for example, 3 or fewer moles of fatty acid per mole of BHMT, while it is difficult to obtain clear formulations with higher fatty acid levels of the polyester quat component, 3.5 or greater moles of fatty acid per mole of BHMT, even at low concentrations.

Example 14

This example illustrates formulations of compounds according to the present invention that are formulated into a microemulsion. As noted above, such formulations generally include three components: (a) compound of structural formula (1), (b) a solvatrope or coupling agent and blends thereof, and (c) an oil or hydrophobic organic component and blends thereof, which are blended in water.

Suitable solvatropes or coupling agents may be selected from the diols and alkoxylates corresponding to structural formulas (T) or (E), TMPD, TMPD alkoxylates, ethanol, isopropanol, butanol, 1,2-cyclohexanedimethanol (1,2-CHDM), 1,4-cyclohexanedimethanol (1,4-CHDM), HPHP glycol, isopentyldiol, 1,2-hexanediol, ethylene glycol butyl ether, hexylene glycol, 2-butoxyethanol (sold by Union Carbide under the tradename butyl CELLOSOLVE®), $C_6$–$C_{12}$ diols/triols and ester diols/triols, glycol ethers, and the like. Oils and hydrophobic organic components may be selected from the fatty $C_8$–$C_{22}$ methyl esters, such as methyl oleate, mineral seal oils, silicone oils, fatty acids, monoglycerides, diglycerides, triglycerides, dialkyl esters, and the like, depending on the application. The methyl esters are the preferred oil based on performance and biodegradability, although mineral seal oil is preferred in car drying aid applications.

An example of such a microemulsion is the following formulation.

EXAMPLE 14

Microemulsion Formulation

| Component | Amount (wt. %) |
|---|---|
| HMDA + 4 moles EO + 2 moles tallow fatty acid + 2 moles DMS | 15 |
| Isopropanol | 2.6 |
| TMPD/CHDM (80%/20%) | 11.7 |
| Methyl oleate | 18.0 |
| Fragrance, dye, preservative, and other additives | as needed |
| Deionized water | to 100 |

Example 15

This example illustrates formulations of compounds according to structural formula (1) for use as emulsifiers, for example, for agricultural emulsifiers or asphalt emulsifiers. In a typical formulation, HMDA is ethoxylated using 4 moles of ethylene oxide per mole of HMDA. The resulting HMDA ethoxylate is esterified with 1.5 to 2 moles of tallow fatty acid per mole of HMDA and the resulting HMDA ethoxylated ester is quaternized with 2 moles of DMS. The HMDA ethoxylated ester quat therefore contains only 1.5 to 2 ester groups per HMDA molecule. This HMDA compound is therefore less hydrophobic than many of the other examples of compounds according to structural formula (1) given in other Examples for other applications. Thus, this compound is useful as an emulsifier for organic compounds, for example, when formulated with pesticides, other surfactants and dispersants, and water, the resulting formulation would make a useful agricultural pesticide spray, the HMDA ethoxylated ester quat encouraging the organic components to remain dispersed in the water, allowing efficient transfer and coverage in treating plants. Examples 16 to 18 provide further examples of this use of the compounds of structural formula (1) and formulations thereof. As can be appreciated, for these applications the polyquaternary compound is prepared having only about 1 to about 2 ester groups per molecule to ensure that the molecule as a whole is less hydrophobic than those that would typically be used in other applications.

Example 16

This example illustrates formulations of compounds according to structural formula (1) for use as a herbicide emulsion agent. A compound according to structural formula (1), for example, HMDA+12 moles EO+1.2 moles canola fatty acid, or mixture thereof is added to a solvent or solvent mixture and water and a herbicide is incorporated therein and an emulsion formed. The amount of the polyquaternary compound is generally from about 5 wt. % to about 50 wt. %, preferably from about 10 wt. % to about 40 wt. %, most preferably from about 15 wt. % to about 30 wt. %, of the herbicide concentrate composition. A typical formulation might be:

EXAMPLE 16

Herbicide Concentrate Emulsion Formulation

| Component | Amount (wt. %) |
|---|---|
| HMDA + 12 moles EO + 1.2 moles canola fatty acid | 20.0 |
| Propylene glycol | 4.0 |
| Water | 2.0 |
| $C_{10}$–$C_{12}$ alcohol + 9 moles EO | 3.0 |
| Glufosinate herbicide | 71.0 |

Example 17

This example illustrates formulations of compounds according to structural formula (1) for use as a pesticide emulsion agent formulation. Unlike Example 16, Example 17 does not incorporate the pesticide itself, instead an appropriate amount of pesticide must be added to the pesticide emulsion agent formulation to make a pesticide emulsion concentrate, which is diluted with water by the user and applied in the dilute form. In general, only 10–30 wt. % of the pesticide emulsion agent formulation is used to in the pesticide emulsion concentrate, that is, there is 70–90 wt. % pesticide in the pesticide emulsion concentrate, which is the form it will generally be commercialized. The final customer will then dilute the pesticide emulsion concentrate (pesticide/emulsifier package) into water for actual application of pesticide.

In such a pesticide emulsion agent formulation, a compound according to structural formula (1), for example, BHMT+15 moles EO+1.2 moles canola fatty acid, or mixture thereof is added to a solvent or solvent mixture and water and a pesticide is incorporated therein and an emulsion formed. The amount of the polyquaternary compound is generally from about 20 wt. % to about 70 wt. %, preferably from about 15 wt. % to about 50 wt. %, most preferably from about 20 wt. % to about 40 wt. %, of the pesticide emulsion agent composition. A typical emulsion agent formulation might be:

EXAMPLE 17

Pesticide Emulsion Agent Formulation

| Component | Amount (wt. %) |
|---|---|
| BHMT + 15 moles EO + 1.2 moles canola fatty acid | 40.0 |
| Phosphate ester | 6.0 |
| Water | 2.0 |
| $C_{10}$–$C_{12}$ alcohol + EO/PO block copolymer | 52.0 |

Example 18

As noted above, the compounds of structural formula (1) may also be used as an asphalt emulsifier as an additive for asphalt. As with the previous emulsifier formulations, the compound of structural formula (1) is prepared having only about 1 to about 2 ester groups per molecule to ensure that the molecule as a whole is less hydrophobic than those that would typically be employed in other applications. If the resulting compound is not quaternized or quaternized to a limited extent, for example, only 1 mole of DMS per mole of HMDA, the possible applications in asphalt products are as a cationic rapid set (CRS) emulsion for chip seal, as a cationic medium set (CMS) for mixing grade applications, in a slurry seal or microsurfacing application, or in a roofing and driveway sealer. The amount of the compound of structural formula (1) in such an application would likely include from about 0.15 wt. % to about 2.0 wt. %, preferably about 0.20 wt. % to about 0.75 wt. %, and most preferably about 0.25 wt. % to about 0.65 wt. %, of the asphalt. Generally the fatty amine should be protonated in order to dissolve in the water. The pH of the emulsifier solution should be less than about 6.5, and may be adjusted with any strong acid to have a pH of between about 1.0 and about 5.0, preferably between about 2.0 to about 4.0, most preferably between about 2.0 and about 3.0.

If the compound is quaternized, for example, with 2 or more moles of DMS per mole of HMDA, the possible applications in asphalt products are as a cationic slow set emulsion, cationic quick set emulsion, tack coat, fog seal, base stabilization, prime coat, slurry seal, microsurfacing, industrial asphalt emulsion, or filled asphalt emulsion. The amount of the compound of structural formula (1) in such an application would likely include from about 0.1 wt. % to about 8.0 wt. %, preferably about 0.20 wt. % to about 5.0 wt. %, and most preferably about 0.5 wt. % to about 2.0 wt. %, of the asphalt. Generally the fatty amine should be protonated in order to dissolve in the water. The pH of the emulsifier solution should be less than about 7.0, and may be adjusted with any strong acid to have a pH of between about 1.0 and about 5.0, preferably between about 2.0 to about 4.0, most preferably between about 2.0 and about 3.0.

Example 19

This example illustrates formulations of compounds according to structural formula (1) for use in corrosion inhibition, for example, for lubricating oil or oil field use. A compound according to structural formula (1), for example, HMDA+4 moles EO+2 moles canola fatty acid, or mixture thereof is added to lubricating or other oils as a corrosion inhibitor. The polyamine may be used alone or in combination with a surfactant and/or coupling agent, which may be incorporated with the polyamine in a formulation or applied separately. When used, an effective amount is applied to the oil or oil mixture that will come in contact with the metal. The term "effective amount" denotes the amount of polyamine compound that would be effective to inhibit corrosion. In general, the amount of the polyamine compound ranges from about 0.001 wt. % to about 5 wt. %, preferably from about 0.01 wt. % to about 1 wt. %, most preferably from about 0.01 wt. % to about 0.5 wt. %, of the oil mixture in which it is used.

Example 20

This example illustrates formulations of compounds according to structural formula (1) for use in a lubricant and anti-balling agent for silicate muds and other water-based muds, for example, to lubricate drill strings to prevent stuck pipe, bit-balling, or string balling associated with drilling wells. The apparatus for drilling and general lubrication processes in well-known to those of skill in the art, and are disclosed, for example, in U.S. Pat. Nos. 5,586,608; 5,593, 954; and 5,639,715, all of these patents being herein incorporated by reference in their entireties. In this lubrication process, a compound according to structural formula (1), for example, BHMT+5 moles EO+2.5 moles canola fatty acid, or mixture thereof is added to lubricating or other oils effective to inhibit stuck pipe, bit balling, or string balling. The polyamine may be used alone or in combination with a surfactant and/or coupling agent, for example, propylene glycols or ethoxylated glycols, which may be incorporated with the polyamine in a formulation or applied separately. Of particular use are the oilfield products available from Witco Corporation under the tradename WITBREAK™, such as WITBREAK™ DPG-484. When used, an effective amount of polyamne is applied to the lubricant mixture as used in the drilling operation. The term "effective amount" denotes the amount of polyamine compound that would be effective to inhibit stuck pipe, bit balling, or string balling. In general, the amount of the polyamine compound ranges from about 0.001 wt. % to about 5 wt. %, preferably from about 0.01 wt. % to about 2 wt. %, most preferably from about 0.05 wt. % to about 0.5 wt. %, of the lubricating mixture in which it is used. If used in a formulation, a typical formulation might be:

EXAMPLE 20

Lubricant and Anti-Balling Agent Formulation

| Component | Amount (wt. %) |
|---|---|
| BHMT + 5 moles EO + 2.5 moles canola fatty acid | 50 |
| Surfactant or coupling agent | 50 |

Example 21

This example illustrates formulations of compounds according to structural formula (1) for use as a mineral and coal dewatering agent, for example, for removal of water by means of a filtration dewatering apparatus known to those of skill in the art. In this process, a compound according to structural formula (1), for example, HMDA+4 moles EO+3 moles tallow fatty acid+2 moles DMS, or mixture thereof is added to the mineral slurry prior to mechanical dewatering, the process becoming more effective as a result. The amount of the polyquaternary compound is generally from about 20 wt. % to about 95 wt. %, preferably from about 30 wt. % to about 80 wt. %, most preferably from about 50 wt. % to about 75 wt. %, of the dewatering agent formulation. A typical formulation might be:

EXAMPLE 21

Mineral and Coal Dewatering Agent Formulation

| Component | Amount (wt. %) |
|---|---|
| HMDA + 4 moles EO + 3 moles tallow fatty acid + 2 moles DMS | 70.0 |
| TMPD + 1 mole EO | 20.0 |
| Nonionic surfactant | 10.0 |

Examples 22–25

These examples illustrate formulations of compounds according to structural formula (1) for use as softener/debonding agents, for example, in tissue or paper products. Examples 22 to 24 are specific examples, while Example 24 presents a general softener/debonder formulation according to the present invention. Example 22 was a thick liquid while Examples 23 and 24 were both clear liquids; all of Examples 22 to 24 were easy to disperse in water.

EXAMPLE 22

Softening/Debonding Agent Formulation for Paper

| Component | Amount (wt. %) |
|---|---|
| HMDA + 4 EO + 1.5 moles tallow fatty acid + 1.5 moles canola fatty acid + 1.75 moles DMS | 80 |
| Propylene glycol | 5 |
| Alkoxylated fatty acid (nonionic surfactant) | 15 |

EXAMPLE 23

Softening/Debonding Agent Formulation for Paper

| Component | Amount (wt. %) |
|---|---|
| HMDA + 4 EO + 3 moles canola fatty acid + 1.5 moles DMS | 80 |
| Propylene glycol | 5 |
| Alkoxylated fatty acid (nonionic surfactant) | 15 |

EXAMPLE 24

Softening/Debonding Agent Formulation for Paper

| Component | Amount (wt. %) |
|---|---|
| HMDA + 10 EO + 1.5 moles tallow fatty acid + 1.5 moles canola fatty acid + 1.5 moles DMS | 80 |
| Propylene glycol | 5.0 |
| Alkoxylated fatty acid (nonionic surfactant) | 15 |

In general, the softener/debonder formulation of the present invention would include the components set forth in Example 25 in the amounts shown.

EXAMPLE 25

General Softener/Debonder Concentrate Formulation

| | Amount (wt. %) | | |
|---|---|---|---|
| Component | typical | preferred | most preferred |
| Compound of structural formula (1) | 10–90 | 30–80 | 60–80 |
| Propylene glycol | 0–30 | 0–20 | 0–10 |
| Polyethylene glycol | 0–30 | 0–20 | 0–10 |
| Nonionic surfactant such as alkoxylated fatty acid or alkoxylated nonionic surfactant | 10–80 | 10–60 | 10–40 |

In the following tests, the performance of formulations of the present invention were compared to the performance of a commercial product available from Witco Corporation under the tradename AROSURF® PA-801, at dosages corresponding to 1, 3, and 5 lb. (#) debonder/ton of fiber using a softwood (SW) fiber furnish. Standard preparation and test methods were employed to prepare handsheets and to conduct the comparative tests against AROSURF PA-801; they are as follows: handsheet preparation (TAPPI test method T-205); dry tensile (TAPPI test method T-492); sorptive rate and capacity (TAPPI test method T-561); paper conditioning (TAPPI test method T-402); and grammage and thickness (TAPPI test method T-220). Softness was evaluated using paired comparison softness panels.

In each case, a dispersion of the appropriate formulation was prepared in water at 25–30° C. An aqueous slurry of SW fibers was treated with the dispersion of the respective formulation at dosages corresponding to 1, 3, and 5 lb. (#) debonder/ton of fiber. Tissue weight handsheets, approximately 60 g/m², were prepared according TAPPI procedure T-205. The handsheets were equilibrated under conditions specified in TAPPI Method T-402. The handsheets were tested for tensile and sorptive rate and capacity according to TAPPI Methods T-492 and T-561, respectively. The results are presented in Table II. In each case the softness of the product treated with Examples 22 to 24 was better than the product treated with a comparable amount of AROSURF® PA-801 debonder.

TABLE II

Testing Results

| Debonder | Tensile strength (kNm/kg) | | | Absorbency Capacity at 0–5 sec (g/g/sec) | | | Absorbency Capacity at 20 sec., (gH₂O/g fiber) | | |
|---|---|---|---|---|---|---|---|---|---|
| used | 1#/ton | 3#/ton | 5#/ton | 1#/ton | 3#/ton | 5#/ton | 1#/ton | 3#/ton | 5#/ton |
| Blank | 15.28 | 15.28 | 15.28 | 0.19 | 0.19 | 0.19 | 2.08 | 2.08 | 2.08 |
| AROSURF ® PA-801 | 13.61 | 10.05 | 7.67 | 0.16 | 0.13 | 0.13 | 1.80 | 1.39 | 1.34 |
| Example 22 | 13.27 | 9.83 | 7.99 | 0.16 | 0.13 | 0.11 | 1.83 | 1.40 | 1.26 |
| Example 23 | 13.30 | 10.32 | 7.83 | 0.15 | 0.13 | 0.13 | 1.76 | 1.51 | 1.43 |
| Example 24 | 12.20 | 10.11 | 8.61 | 0.16 | 0.13 | 0.13 | 1.68 | 1.40 | 1.36 |

From these tests and the results presented in Table II, it can be seen that HMDA ester quats are effective debonders and compare favorably in performance to an industry standard. Indeed, the HMDA ester quats afford debonded tissue products with good absorbency rates and capacities and hand panels confirm that the formulations of the instant invention give better softness than AROSURF® PA-801 debonder. In addition, the HMDA ester quat formulations have low odor and each of the above formulations was easy to disperse in warm water. As with all of the Examples given, Examples 22 to 25 are only exemplary and, although applied here to softwood fibers, may be used with hardwood fiber, recycled fiber, baggasse fibers, fluff pulp, and all natural papermaking fibers and blends thereof.

Example 26

This example illustrates formulations of compounds according to structural formula (1) for use as deinking agents, for example, in recycled paper products. Generally such formulations are added to the pulper and/or to the slurry passing into the flotation cell. Furnishes that may be deinked with the compounds of the instant invention include waste paper with laser print, printed waste paper for a newsprint mill, ink fixed on pulp fiber of the printed waste paper product such as newspaper and magazines, and flexo news/magazine/newsprint, and the like.

The apparatus and processes for deinking operation in well-known to those of skill in the art. Typical apparatus and processes are disclosed in U.S. Pat. Nos. 5,622,597; 5,346,543; and 5,696,292, all of which are hereby incorporated by reference in their entireties. Additional apparatus and methods are disclosed in PCT WO/95/12026 and EP 0 726 246 A1, both of which are hereby incorporated by reference in their entireties.

In such a deinking process, the amount of the compound of structural formula (1) is about 0.01 wt. % to about 2.0 wt. %, preferably about 0.03 wt. % to about 1.0 wt. %, and most preferably about 0.05 wt. % to about 0.5 wt. % of the dry fiber. Other additives typically used include an ethylene oxide/propylene oxide nonionic (for example, alcohol or fatty acid alkylphenol derivatives) surfactant for frothing and foam control, sodium silicate, sodium hydroxide, hydrogen peroxide or sodium hypochlorite, and an EDTA or DTPA chelant. In addition, such cationic deinking agents can be combined with fatty acids, alkylene oxide adducts, and other solvents. Deinking is usually conducted on fiber slurries of 1% consistency at 40–50° C.

Examples 27 to 31

These examples illustrate formulations of compounds according to structural formula (1) for use in personal care formulations, for example, for hair conditioners and skin conditioners. Example 29 is a microemulsion example comparable to Example 14.

EXAMPLE 27

HMDA Hair Conditioner Formulation

| Component | Amount (wt. %) |
|---|---|
| HMDA + 4 moles EO + 2 moles canola fatty acid + 2 moles DMS | 1.18 |
| Cetyl Alcohol | 2.00 |
| Ceteareth-20 (cetearyl alcohol ethoxylated with 20 moles of EO), available from Witco Corporation under the tradename VARONIC ® 63-E20 | 1.00 |
| Fragrance, dye, preservative, and other additives | as needed |
| Deionized water | to 100 |

EXAMPLE 28

BHMT Hair Conditioner Formulation

| Component | Amount (wt. %) |
|---|---|
| BHMT + 5 moles EO + 3.5 moles canola fatty acid + 2.5 moles DMS | 1.18 |
| Cetyl Alcohol | 2.00 |
| Ceteareth-20 (cetearyl alcohol ethoxylated with 20 moles of EO), available from Witco Corporation under the tradename VARONIC ® 63-E20 | 1.00 |
| Fragrance, dye, preservative, and other additives | as needed |
| Deionized water | to 100 |

EXAMPLE 29

BHMT Microemulsion Hair Conditioner Formulation

| Component | Amount (wt. %) |
|---|---|
| BHMT + 5 moles EO + 3.5 moles canola fatty acid + 2.5 moles DMS | 1.8 |

EXAMPLE 29-continued

BHMT Microemulsion Hair Conditioner Formulation

| Component | Amount (wt. %) |
|---|---|
| Mineral oil (available from Witco Corporation under the tradename KAYDOL ®) | 1.8 |
| TMPD + 1 EO | 1.2 |
| Fragrance, dye, preservative, and other additives | as needed |
| Deionized water | to 100 |

In hair swatch tests, the compositions of Examples 27 to 29 perform significantly better than comparable formulations using dicetylamimonium chloride in place of the HMDA ester quat or BHMT ester quat, exhibiting improved comb and detangle properties, shine, and feel on hair. In addition, the compositions of Examples 27 to 29 were non-irritating while comparable formulations using dicetylammonium chloride caused severe redness, bum, and itch sensations, unacceptable in a personal care formulation. As with the microemulsion example of Example 14, personal care microemulsion formulations such as Example 29, include three components: (a) compound of structural formula (1), (b) a solvatrope or coupling agent and blends thereof, and (c) an oil or hydrophobic organic component and blends thereof, which are blended in water. In such a formulation the amount of the compound of structural formula (1) is about 0.1 wt. % to about 65 wt. % of the formulation, preferably about 0.1 wt. % to about 35 wt. %, and most preferably about 0.1 wt. % to about 5 wt. %; the amount of solvatrope or coupling agent is about 0.1 wt. % to about 65 wt. % of the formulation, preferably about 0.1 wt. % about 35 wt. %, and most preferably about 0.1 wt. % to about 5 wt. %; the amount of oil or hydrophobic organic component is about 0.1 wt. % to 65 wt. % of the formulation, preferably about 0.1 wt. % to about 35 wt. %, and most preferably about 0.1 wt. % to about 5 wt. %; and the amount of water is about 20 to 99.7 wt. % of the formulation, preferably about 35 wt. % to about 99.7 wt. %, and most preferably about 65 wt. % to about 99.7 wt. %. Suitable solvatropes or coupling agents may be selected from the diols and alkoxylates corresponding to structural formulas (T) or (E), hydroxypivalyl hydroxypivalate and its alkoxylated derivatives, TMPD, TMPD alkoxylates, ethanol, isopropanol, butanol, 1,2-cyclohexanedimethanol (1,2-CHDM), 1,4-cyclohexanedimethanol (1,4-CHDM), HPHP glycol, isopentyldiol, 1,2-hexanediol, ethylene glycol butyl ether, hexylene glycol, isoprene glycol (3-methyl-1,3-butanediol), sorbitan ethoxylates, 2-butoxyethanol (sold by Union Carbide under the tradename butyl CELLOSOLVE®), $C_6$–$C_{12}$ diols/triols and ester diols/triols and their alkoxylated derivatives, glycol ethers, and the like. Oils and hydrophobic organic components may be selected from the fatty $C_8$–$C_{12}$ methyl esters, such as methyl oleate, mineral seal oils, silicone oils, fatty acids, monoglycerides, diglycerides, triglycerides, dialkyl esters, and the like, depending on the application.

Examples 30 and 31 provide examples of suitable hand lotions or skin conditioners.

EXAMPLE 30

HMDA Skin Conditioner Formulation

| Component | Amount (wt. %) |
|---|---|
| HMDA + 4 moles EO + 2 moles canola fatty acid + 2 moles DMS | 1.18 |
| Glyceryl stearate | 1.00 |
| Stearic acid | 2.00 |
| Cetyl alcohol | 2.00 |
| Glycerine (available from Witco Corporation under the tradename KEMSTRENE ®) | 1.60 |
| Mineral oil (available from Witco Corporation under the tradename KAYDOL ®) | 6.00 |
| PEG-30 glyceryl cocoate (available from Witco Corporation under the tradename VARONIC ® LI-63) | 1.60 |
| Fragrance, dye, preservative, and other additives | as needed |
| Deionized water | to 100 |

EXAMPLE 31

BHMT Skin Conditioner Formulation

| Component | Amount (wt. %) |
|---|---|
| BHMT + 5 moles EO + 3.5 moles canola a fatty acid + 2.5 moles DMS | 1.18 |
| Glyceryl stearate | 1.00 |
| Stearic acid | 2.00 |
| Cetyl alcohol | 2.00 |
| Glycerine (available from Witco Corporation under the tradename KEMSTRENE ®) | 1.60 |
| Mineral oil (available from Witco Corporation under the tradename KAYDOL ®) | 6.00 |
| PEG-30 glyceryl cocoate (available from Witco Corporation under the tradename VARONIC ® LI-63) | 1.60 |
| Fragrance, dye, preservative, and other additives | as needed |
| Deionized water | to 100 |

It is understood that many of the examples and claims presented include components that are salts, that is, they include an anion and a cation. It is understood by those of skill in the art that the identity of the anion or cation of a given compound may not be crucial in the activity of the compound for a given purpose (that is, it may constitute a spectator ion) and an appropriate substitute may be made therefor. Thus, with regard to the compounds of structural formula (1), the counter anion $A^-$ may be, for example, chloride, bromide, methyl sulfate, ethyl sulfate, or salicylate or the like. Similarly, the sodium ion present in many of the anionic surfactants claimed and presented in the examples above may be replaced by other cations, such as potassium ion or ammonium ion, without appreciably affecting the performance of the anionic surfactant. Furthermore, with regard to the other components that may be salts that are be added to the composition or subsequently added to the composition, for example, viscosity modifiers, the component includes all similar compounds, that is, compounds where the ions are substituted by any other ion which is not significantly deleterious to the desired chemical or physical properties of the overall compound in its intended use. It is therefore understood that such ion substitution is well-known in the art and all such possibilities and equivalents are intended to be embraced within the appended claims.

As noted above, the examples provided are intended to further describe the aspects of the present invention. The examples are illustrative only and are not to be construed as limiting the scope of that which is regarded as the invention. Therefore, the scope of the present invention is only to be limited by the following claims and the equivalents thereto.

In the specification and claims, the terms "comprise", "comprising", or "comprises" are intended to convey that the composition or formulation has or includes the recited components, but does not exclude other non-recited components.

What is claimed is:

1. A composition comprising:
   (a) a compound of the following structural formula (1):

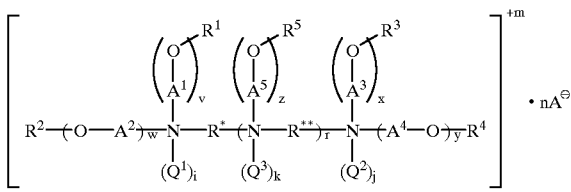

wherein each R* and R** is independently a linear, branched or cyclic alkylene group containing 6 to 12 carbon atoms, wherein no two nitrogen atoms are separated by fewer than 6 carbon atoms;
   each of $A^1$, $A^2$, $A^3$, $A^4$, and $A^5$ is independently a straight or branched alkylene containing 2 to 4 carbon atoms;
   each of $R^1$, $R^2$, $R^3$, $R^4$, and $R^5$ is independently —H or $R^AC(O)$— wherein $R^A$ is straight or branched alkyl group or alkenyl group containing 7 to 21 carbon atoms and having 0 to 4 carbon—carbon double bonds; provided that at least three of $R^1$, $R^2$, $R^3$, $R^4$, or $R^5$ is $R^AC(O)$—; each of $Q^1$, $Q^2$, and $Q^3$ is independently —$CH_3$, —$C_2H_5$—, —$C_3H_7$—, —$C_4H_5$—, benzyl, —$CH_2COOH$, or —$CH_2COOA^-$;
   m is 0 to 4;
   r is 0 to 2;
   each v, w, x, y, and z is independently 1 to 8;
   i is 0 to 1, j is 0 to 1, and each k is 0 to 1, and the sum of
   (i+j+k) is 2.0 to 3, or when r=2, then the sum of (i+j+2k) is 2.0 to 4; each A is independently an anion; and
   n is the number of moles of A needed to give the compound of structural formula (1) a zero net charge, with the proviso that when r=1 or 2, each $A^1$, $A^2$, $A^3$, $A^4$, and $A^5$ is a branched alkylene and when r=0, each $A^1$, $A^2$, $A^3$, $A^4$, and $A^5$ is independently a straight alkylene group; and
   (b) a second surfactant selected from the group consisting of anionic surfactants, cationic surfactants, zwitterionic surfactants, nonionic surfactants, amphoteric surfactants and blends thereof.

2. The composition according to claim 1, wherein the composition further comprises water.

3. The composition according to claim 1, wherein the second surfactant comprises a conventional quaternary compound.

4. The composition according to claim 3, wherein the composition does not contain a silicone.

5. The composition according to claim 3, wherein the composition comprises a mixture of two or more different compounds of structural formula (1).

6. The composition according to claim 3, wherein the composition comprises a mixture of two or more different conventional quaternary compounds.

7. The composition according to claim 3, wherein m is from about 1 to 4.

8. The composition according to claim 3, wherein at least one of v, w, x, y, and z is greater than 1.

9. The composition according to claim 8, wherein each of v, w, x, y, and z is greater than 1.

10. The composition according to claim 1, wherein the secondary surfactant is selected from the group consisting of: akylbenzene sulfonates, α-olefin sulfonates, and xylene sulfonates.

11. The composition according to claim 1, wherein the secondary surfactant is selected from the group consisting of: nonylphenol ethoxylates; $C_5$–$C_{20}$ linear or branched alkoxylates using EO, PO, iPO, BO, or mixtures thereof; amine ethoxylates; fatty amide ethoxylates; fatty acid ethoxylates; carboxylated nonionics; α-polyglucosides; and mixtures thereof.

12. The composition according to claim 1, wherein the secondary surfactant is selected from the group consisting of: ammonium lauryl sulfate, sodium lauryl sulfate, any α-olefin sulfonate, ammonium laureth sulfate (2 or 3 moles), sodium laureth sulfate (2 or 3 moles), sodium myristyl sulfate, sodium myristeth sulfate (1–4 moles), ammonium xylene sulfonate, sodium xylene sulfonate, TEA dodecylbenzene sulfonate, TEA lauryl sulfate, ammonium pareth sulfate, sodium pareth sulfate, sodium oleth sulfate, derivatives thereof, and mixtures thereof.

13. The composition according to claim 1, wherein the secondary surfactant is selected from the group consisting of: betaines, sulfosuccinates, mono- and diglycerides, glycinates, sugars and derivatives thereof, hydroxysultaines, mono- and diacetates, ethoxylated derivatives thereof, and mixtures thereof.

14. The composition according to claim 13, wherein the secondary surfactant is selected from the group consisting of: cocamidopropyl betaine, lauramidopropyl betaine, ricinoleamidopropyl betaine, myristamidopropyl betaine, palmamidopropyl betaine, stearamidopropyl betaine, behenamidopropyl betaine, erucamidopropyl betaine, cocamidopropyl hydroxysultaine, myristamidopropyl hydroxysultaine, palmamidopropyl hydroxysultaine, stearamidopropyl hydroxysultaine, behenamidopropyl hydroxysultaine, erucamidopropyl hydroxysultaine, disodium lauroamphodiacetate, disodium cocamphodiacetate, disodium myristamphodiacetate, disodium palmamphodiacetate, disodium stearamphodiacetate, disodium behenamphodiacetate, disodium erucamphodiacetate, sodium lauryl amphoacetate, sodium cocamphoacetate, sodium cocoamphopropionate, sodium laurylamphopropionate, disodium lauroamphodipropionate, sodium lauryl sulfosuccinate, disodium laureth sulfosuccinate, cocobetaine, laurylbetaine, myristylbetaine, stearylbetaine, behenylbetaine, PEG 1-300 glyceryl cocoate, PEG 1-300 glyceryl tallowate, PEG 1-500 hydrogenated glyceryl palmitate, coco-glucoside, lauryl glucoside, decyl glucoside, and mixtures thereof.

15. The composition according to claim 1, wherein the secondary surfactant is an alkanolamide selected from the group consisting of: almondamide DEA, behenamide DEA, cocamide DEA, hydrogenated tallowamide DEA, isostearamide DEA, lactamide DEA, lauramide DEA, linoleamide DEA, myristamide DEA, oleamide DEA, palmamide DEA, palmitamide DEA, ricinoleamide DEA, soyamide DEA, stearamide DEA, tallamide DEA, tallowamide DEA, acetamide MEA, behenamide MEA, cocamide MEA, hydroxystearamide MEA, isostearamide MEA, lactamide MEA, lauramide MEA, linoleamide MEA, myristamide MEA, oleamide MEA, palmamide MEA, palmitamide MEA, ricinoleamide MEA, stearamide MEA, tallowamide MEA, undecylenamide MEA, cocamide MIPA, hydroxyethyl stearamide MIPA, isostearamide MIPA, lauramide MIPA, linoleamide MIPA, myristamide MIPA, oleamide MIPA, palmamide MIPA, ricinoleamide MIPA, stearamide MIPA, and mixtures thereof.

16. The composition according to claim 1, wherein the secondary surfactant is an amine oxide selected from the group consisting of: behenamine oxide, cocamidopropylamine oxide, cocamine oxide, decylamine oxide, dihydroxyethylcocamine oxide, dihydroxyethyllauramine oxide, dihydroxyethyltallowamine oxide, hydrogenated palm kernel amine oxide, hydrogenated tallowamine oxide, isostearamidopropylamine oxide, lauramidopropylamine oxide, lauramine oxide, myristamidopropylamine oxide, myristamine oxide, oleamidopropylamine oxide, oleamine oxide, palmitamidopropylamine oxide, palmitamine oxide, soyamidopropylanine oxide, stearamidopropylamine oxide, stearamine oxide, tallowamidopropylamine oxide, tallowamine oxide, undecylenamidopropylamine oxide, and mixtures thereof.

17. The composition according to claim 1 wherein said compound of formula (1) is a hexamethylenediamine alkoxylated ester diamine or a bis(hexamethylenediamine) triamine alkoxylated ester.

* * * * *